US009663445B2

(12) United States Patent
Hattori et al.

(10) Patent No.: US 9,663,445 B2
(45) Date of Patent: May 30, 2017

(54) SYNTHESIS SYSTEM, RUBBER CHEMICAL SUBSTANCE FOR TIRES, SYNTHETIC RUBBER FOR TIRES, AND PNEUMATIC TIRE

(71) Applicant: SUMITOMO RUBBER INDUSTRIES, LTD., Kobe-shi, Hyogo (JP)

(72) Inventors: Takayuki Hattori, Kobe (JP); Takao Wada, Kobe (JP); Keitaro Fujikura, Kobe (JP); Yuka Yokoyama, Kobe (JP); Toshiro Matsuo, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 0 days.

(21) Appl. No.: 14/801,001

(22) Filed: Jul. 16, 2015

(65) Prior Publication Data
US 2015/0315125 A1 Nov. 5, 2015

Related U.S. Application Data

(62) Division of application No. 13/637,336, filed as application No. PCT/JP2012/051503 on Jan. 25, 2012, now Pat. No. 9,115,047.

(30) Foreign Application Priority Data

Jan. 26, 2011 (JP) ................. 2011-014494
Jan. 26, 2011 (JP) ................. 2011-014495

(51) Int. Cl.
| | | |
|---|---|---|
| C07C 15/46 | (2006.01) |
| C07C 211/46 | (2006.01) |
| C07C 209/04 | (2006.01) |
| C07C 37/16 | (2006.01) |
| B01J 29/40 | (2006.01) |
| B01J 29/46 | (2006.01) |
| B01J 29/48 | (2006.01) |
| B60C 1/00 | (2006.01) |
| C07C 1/20 | (2006.01) |
| C07C 201/08 | (2006.01) |
| C07C 209/36 | (2006.01) |
| C12P 7/22 | (2006.01) |
| C12P 7/28 | (2006.01) |
| C07C 1/22 | (2006.01) |
| C08F 236/10 | (2006.01) |
| C08G 73/02 | (2006.01) |
| C08L 9/06 | (2006.01) |
| C07C 209/18 | (2006.01) |
| C07C 1/24 | (2006.01) |
| C07C 2/68 | (2006.01) |

(52) U.S. Cl.
CPC .......... C07C 209/04 (2013.01); B01J 29/40 (2013.01); B01J 29/46 (2013.01); B01J 29/48 (2013.01); B60C 1/0016 (2013.04); C07C 1/20 (2013.01); C07C 1/22 (2013.01); C07C 1/24 (2013.01); C07C 2/68 (2013.01); C07C 15/46 (2013.01); C07C 37/16 (2013.01); C07C 201/08 (2013.01); C07C 209/18 (2013.01); C07C 209/36 (2013.01); C07C 211/46 (2013.01); C08F 236/10 (2013.01); C08G 73/02 (2013.01); C08L 9/06 (2013.01); C12P 7/22 (2013.01); C12P 7/28 (2013.01); C07C 2521/04 (2013.01); C07C 2527/126 (2013.01); C07C 2529/18 (2013.01); C07C 2529/40 (2013.01); C08L 2205/025 (2013.01); C08L 2205/03 (2013.01); C12P 2203/00 (2013.01); Y02P 20/52 (2015.11)

(58) Field of Classification Search
CPC ............ C07C 209/04; C07C 1/22; C07C 2/68
See application file for complete search history.

(56) References Cited

U.S. PATENT DOCUMENTS

| | | |
|---|---|---|
| 2008/0242823 A1 | 10/2008 | Fujikura |
| 2009/0306431 A1 | 12/2009 | Fujikura |
| 2010/0185033 A1 | 7/2010 | Karim et al. |

FOREIGN PATENT DOCUMENTS

| | | |
|---|---|---|
| CN | 101274996 A | 10/2008 |
| CN | 101691589 A | 4/2010 |
| JP | 58-59928 A | 4/1983 |
| JP | 2006-89552 A | 4/2006 |
| JP | 2008-88140 A | 4/2008 |
| JP | 2008-274225 A | 11/2008 |
| JP | 2010-17176 | * 1/2010 |
| JP | 2010-17176 A | 1/2010 |

(Continued)

OTHER PUBLICATIONS

Huang, R., "Development Tendency of the Styrene Production Technology," Lan Hua Technology, 1993, vol. 11, No. 1, pp. 25-30, with English translation.
International Search Report issued in PCT/JP2012/051503 mailed Apr. 24, 2012.

(Continued)

Primary Examiner — Robert Harlan
(74) Attorney, Agent, or Firm — Birch, Stewart, Kolasch & Birch, LLP

(57) ABSTRACT

The present invention provides a synthesis system that can synthesize aniline and/or styrene efficiently, a synthesis system that can synthesize butadiene (1,3-butadiene) efficiently, a rubber chemical for a tire which is synthesized from the aniline obtained by the synthesis system, a synthetic rubber for a tire which is synthesized from the styrene and/or butadiene obtained by the synthesis systems, and a pneumatic tire produced using the rubber chemical for a tire and/or the synthetic rubber for a tire. The present invention relates to a synthesis system for synthesizing aniline and/or styrene from an alcohol having two or more carbon atoms via an aromatic compound.

18 Claims, 4 Drawing Sheets

(56) References Cited

FOREIGN PATENT DOCUMENTS

| JP | 2010-535826 A | | 11/2010 |
|----|---------------|---|---------|
| JP | 2012-153654 A | | 8/2012 |
| JP | 2012-153655 A | | 8/2012 |
| WO | WO 2007/137566 A1 | | 12/2007 |
| WO | WO 2010/145914 | * | 12/2007 |
| WO | WO 2007/137566 | * | 12/2010 |
| WO | WO 2010/145914 A1 | | 12/2010 |

OTHER PUBLICATIONS

Chinese Office Action and Search Report for Chinese Application No. 201410742596.2, dated Feb. 3, 2017, with an English translation thereof.

Xiaoming, "Production, Consumption and Market Analysis of Aniline at Home and Abroad," Journal of Petrochemical Technology, vol. 18, No. 5, Oct. 25, 2002, 7 pages total.

* cited by examiner

SEQUENCE LISTING

```
<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: Synthetic primer

<400> SEQUENCE: 1
gcggtaccat gaactatcct gccgagcc                                        28

<210> SEQ ID NO 2
<211> LENGTH: 29
<212> TYPE: DNA
<213> ORGANISM: Artificial Sequence
<220> FEATURE:
<223> OTHER INFORMATION: Synthetic primer

<400> SEQUENCE: 2
gcggccgctt aaataaagtc aaaacgcgc                                       29
```

SYNTHESIS SYSTEM, RUBBER CHEMICAL SUBSTANCE FOR TIRES, SYNTHETIC RUBBER FOR TIRES, AND PNEUMATIC TIRE

CROSS REFERENCE TO RELATED APPLICATIONS

This application is a Divisional of U.S. application Ser. No. 13/637,336, filed Sep. 25, 2012, which is the U.S. National Phase of PCT/JP2012/051503, filed Jan. 25, 2012, which claims priority under 35 U.S.C. §119(a) to Japanese Patent Application No. JP 2011-014494 filed in Japan on Jan. 26, 2011, and Japanese Patent Application No. JP 2011-014495 filed in Japan on Jan. 26, 2011, the entire contents of which is hereby expressly incorporated by reference.

TECHNICAL FIELD

The present invention relates to a synthesis system that can synthesize aniline and/or styrene efficiently, a synthesis system that can synthesize butadiene (1,3-butadiene) efficiently, a rubber chemical for a tire which is synthesized from the aniline obtained by the synthesis system, a synthetic rubber for a tire which is synthesized from the styrene and/or butadiene obtained by the synthesis systems, and a pneumatic tire produced using the rubber chemical for a tire and/or the synthetic rubber for a tire.

BACKGROUND ART

Aniline, a material for rubber chemicals such as antioxidants, thiazole vulcanization accelerators and sulfenamide vulcanization accelerators; and styrene and butadiene, materials for synthetic rubber such as styrene butadiene rubber and butadiene rubber, are generally synthesized from petroleum. However, fossil fuels such as petroleum and natural gas are going to be depleted, and thus a price hike of fossil fuels is expected in the future. For this reason, consumption of fossil fuels has been demanded to be reduced by increasing the yield or From the viewpoint of utilization of natural resources, a method of synthesizing a vulcanization accelerator is known in which a naturally-derived long chain amine that is synthesized by reductive amination of a saturated or unsaturated fatty acid obtained by hydrolysis of natural fat and oil is used as a material. However, this synthesis method requires mercaptobenzothiazoles or dibenzothiazolyl disulfide in the production process, and these substances are not taught as products from natural resources.

Examples of known synthesis methods using biomass resources as materials include a method of synthesizing an aromatic compound such as benzene from a lower hydrocarbon such as methane contained in biogas. However, since the material is gas and thus difficult to handle, the method is still desired to be improved. Moreover, a method using biomethanol as a material is also known; but this method is still desired to be improved because of high toxicity of the material. Furthermore, it is difficult for either of the methods to ensure a sufficient yield, and thus improvement is still desired on this point.

Patent Literatures 1 and 2 disclose methods of synthesizing aniline from glucose with microorganisms. However, these methods need some improvement in terms of production speed, production scale or the like, and in terms of usability of various microorganism species, and production efficiency. Therefore, an alternative technique has been demanded.

CITATION LIST

Patent Literature

Patent Literature 1: JP-A 2010-17176
Patent Literature 2: JP-A 2008-274225

SUMMARY OF INVENTION

Technical Problem

The present invention aims to solve the above problems and provide a synthesis system that can synthesize aniline and/or styrene efficiently, a synthesis system that can synthesize butadiene (1,3-butadiene) efficiently, a rubber chemical for a tire which is synthesized from the aniline obtained by the synthesis system, a synthetic rubber for a tire which is synthesized from the styrene and/or butadiene obtained by the synthesis systems, and a pneumatic tire produced using the rubber chemical for a tire and/or the synthetic rubber for a tire.

The present invention also aims to provide a synthesis system that can synthesize aniline efficiently using a biomass material, a rubber chemical for a tire which is synthesized from the aniline obtained by the synthesis system, and a pneumatic tire produced using the rubber chemical for a tire.

Solution to Problem

A first aspect of the present invention relates to a synthesis system for synthesizing at least one of aniline and styrene from an alcohol having two or more carbon atoms via an aromatic compound.

The alcohol is preferably ethanol.
The ethanol is preferably bioethanol.
The aromatic compound is preferably benzene.
The benzene is preferably synthesized via at least one of toluene and xylene.
The aromatic compound is preferably synthesized via an alkene.
The synthesis system is preferably adapted to subject the alcohol to catalysis by a solid acid catalyst.
The solid acid catalyst is preferably at least one selected from the group consisting of zeolites, alumina, and titanium compounds.
The solid acid catalyst is preferably an MFI-type zeolite.
The synthesis system is preferably adapted to subject the alcohol to catalysis by a solid acid catalyst to give a reaction product, and circulate the reaction product so that it is further subjected to catalysis by the solid acid catalyst.
The synthesis system is preferably adapted to distill the reaction product, and circulate compounds other than a target product so that they are further subjected to catalysis by the solid acid catalyst.
The synthesis system is preferably adapted to distill the reaction product to give a distillate, cool the distillate to not higher than the melting point of benzene to recover benzene, and circulate compounds other than the benzene so that they are further subjected to catalysis by the solid acid catalyst.
In the synthesis system, the circulation is preferably repeated.

The first aspect of the present invention also relates to a synthesis system for synthesizing butadiene from an alcohol having two or more carbon atoms.

The first aspect of the present invention also relates to a rubber chemical for a tire, synthesized from the aniline obtained by the synthesis system.

The first aspect of the present invention also relates to a synthetic rubber for a tire, synthesized from at least one of the styrene obtained by the synthesis system and the butadiene obtained by the synthesis system.

The first aspect of the present invention also relates to a pneumatic tire produced using at least one of the rubber chemical for a tire and the synthetic rubber for a tire.

A second aspect of the present invention relates to a synthesis system for synthesizing aniline from a biomass material via phenol.

The biomass material is preferably a sugar or bioethanol.

The synthesis system is preferably adapted to produce the phenol by a microorganism. Moreover, the synthesis system is preferably adapted to produce the phenol by liquid culture of a microorganism. Here, the microorganism producing the phenol is preferably resistant to organic solvents.

The synthesis system is preferably adapted to produce the phenol from bioethanol as the biomass material by using a solid acid catalyst. Here, the solid acid catalyst is preferably a zeolite. Moreover, the solid acid catalyst is preferably an MFI-type zeolite.

Furthermore, the solid acid catalyst is preferably an MFI-type zeolite carrying a member selected from the group consisting of simple substances of copper, titanium, platinum and ruthenium, and compounds thereof.

The second aspect of the present invention also relates to a rubber chemical for a tire, synthesized from the aniline obtained by the synthesis system. Here, the rubber chemical for a tire is preferably synthesized by further using acetone obtained from a biomass material.

The acetone is preferably obtained by acetone-butanol fermentation of a sugar by a microorganism. Here, the microorganism preferably belongs to the genus *Clostridium*. Alternatively, the microorganism preferably includes a gene of the genus *Clostridium* introduced thereinto.

The gene preferably encodes acetoacetate decarboxylase (EC4.1.1.4), coenzyme A transferase, or thiolase.

The acetone is preferably obtained by separation from pyroligneous acid. Alternatively, the acetone is preferably derived from bioethanol.

The second aspect of the present invention also relates to a pneumatic tire produced using the rubber chemical for a tire.

Advantageous Effects of Invention

The first aspect of the present invention provides a synthesis system for synthesizing aniline and/or styrene from an alcohol having two or more carbon atoms via an aromatic compound; and a synthesis system for synthesizing butadiene (1,3-butadiene) from an alcohol having two or more carbon atoms. According to the first aspect of the present invention, aniline, styrene, and butadiene can be efficiently synthesized. Therefore, use of at least one selected from the group consisting of the aniline, styrene, and butadiene synthesized by the synthesis systems contributes to reduction in the amount of fossil resources used in the production of rubber chemicals for a tire, synthetic rubbers for a tire, and pneumatic tires.

The second aspect of the present invention provides a synthesis system for synthesizing aniline from a biomass material via phenol. The second aspect of the present invention enables efficient synthesis of aniline in a resource-saving manner without the use of fossil fuels. Therefore, use of the aniline synthesized by the synthesis system contributes to reduction in the amount of fossil fuels used in the production of rubber chemicals for a tire and pneumatic tires.

DESCRIPTION OF EMBODIMENTS

Figure 1:
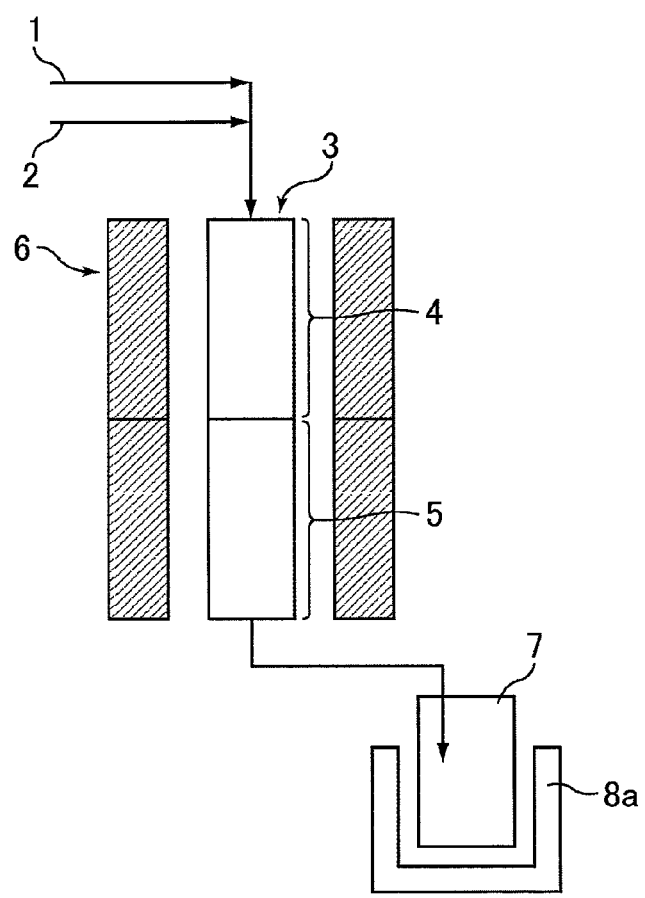
FIG. 1 is a schematic view showing one embodiment of an apparatus for directly synthesizing an aromatic compound from an alcohol.

The first aspect of the present invention relates to a synthesis system (synthesis method) for synthesizing aniline and/or styrene from an alcohol having two or more carbon atoms via an aromatic compound; and a synthesis system (synthesis method) for synthesizing butadiene from an alcohol having two or more carbon atoms.

The alcohol having two or more carbon atoms is not particularly limited, and may be a common one. From the viewpoint of low toxicity, easy transportation, and low cost, alcohols having two to eight carbon atoms are preferred, and ethanol is more preferred. Bioethanol synthesized from a biomass resource can be suitably used as the ethanol because it can be produced without depending on fossil resources, and an increase in the yield of the aromatic compound and alkene can also be expected.

A method for producing bioethanol is explained below.

Bioethanol can be produced by reducing the molecular weight of a biomass resource (e.g. corn, sugar cane, bagasse, kenaf, legumes, straw, wheat straw, rice hulls, thinning residues, waste wood, waste paper, waste pulp, organic urban waste) (Step 1), fermenting the resulting sugars into ethanol (Step 2), and separating and purifying the ethanol (Step 3).

In (Step 1), for example, sugars such as hexoses and pentoses, starch, cellulose, hemicellulose, and lignin are produced from the biomass resource. These products are used directly or after selection for the ethanol fermentation of (Step 2). Starch, cellulose, and hemicellulose are preliminarily saccharified by steam treatment, hydrolysis, enzymatic degradation, or the like, and then used for the ethanol fermentation of (Step 2).

In (Step 2), ethanol is produced from monosaccharides or the like obtained in (Step 1) by utilizing a microorganism. Examples of usable microorganisms include wild strains of yeasts, *Escherichia coli*, and bacteria of the genus *Zymomonas*, and their transfectants.

In (Step 3), the resulting fermentation liquid is separated into solid components and a liquid phase. Thereafter, ethanol is concentrated by repeating evaporation and condensation in a distillation process. Moreover, further concentration using a dehydrating agent or a separation membrane may be performed.

Suitable examples of the method for synthesizing an aromatic compound and/or an alkene from the alcohol include subjecting the alcohol to catalysis by a catalyst. The reaction temperature is preferably 280° C. to 500° C., and more preferably 300° C. to 460° C. The reaction may be performed at either normal or increased pressure (preferably at 0.3 to 3.0 MPaG). The feed rate of the alcohol in terms of LHSV is preferably 0.1 to 3.0/hr, and more preferably 0.5 to 1.5/hr.

Examples of the catalyst include solid acid catalysts such as zeolites, alumina, titanium compounds, sulfate ion-supported zirconia, and $WO_3$-supported zirconia. In particular, in terms of increasing the reaction efficiency, at least one selected from the group consisting of zeolites, alumina, and titanium compounds is preferred. Zeolites are more preferably used alone or in combination with alumina.

In the case of synthesizing an aromatic compound from the alcohol, zeolites are particularly preferred. Moreover, zeolites having below-mentioned molar ratios of $SiO_2$ to $Al_2O_3$ and below-mentioned pore sizes are further preferred because such zeolites enable selective synthesis of target aromatic compounds such as benzene.

In the case of synthesizing an aromatic compound from the alcohol using a combination of alumina and a zeolite, the aromatic compound can be synthesized more economically with higher efficiency by first synthesizing an alkene using alumina and/or a zeolite, and the like, and further subjecting the obtained alkene to catalysis by the zeolite and the like.

In the case of synthesizing an alkene such as ethylene and/or butadiene from the alcohol, alumina and/or a zeolite are/is preferably used.

Zeolites are crystalline aluminosilicates having a microporous structure. Specific examples of zeolites include A-type zeolites, L-type zeolites, X-type zeolites, Y-type zeolites, MFI-type zeolites, MWW-type zeolites, β-type zeolites, mordenite, ferrierite, and erionite. Moreover, zeolites may be used in which aluminum atoms in the zeolite skeleton are substituted with a member selected from the group consisting of metal elements other than aluminum, such as Ga, Ti, Fe, Mn, Zn, B, Cu, Pt, Re, Mo, Gd, Nb, Y, Nd, W, La, and P, and compounds thereof. In particular, in terms of selectively producing benzene and minimizing further secondary reactions such as alkylation, MFI-type ZSM-5 and MWW-type MCM-22 are preferred.

Examples of the MFI-type zeolites include zeolites having MFI (Mobil Five) structure such as ZSM-5, ZSM-8, zeta 1, zeta 3, Nu-4, Nu-5, TZ-1, TPZ-1, and TS-1. From the viewpoint of high selectivity and good reaction efficiency, ZSM-5-type zeolites are particularly preferred among the above examples.

Cations occupying the ion-exchangeable cation sites of zeolite are not particularly limited, and examples thereof include hydrogen ion (proton); alkali metal ions such as lithium ion, sodium ion, and potassium ion; alkaline earth metal ions such as magnesium ion, calcium ion, strontium ion, and barium ion; transition metal ions such as iron ion, and silver ion; and primary to quaternary ammonium ions. In particular, in terms of achieving high reaction efficiency by enhancement of the surface activity, hydrogen ion (proton) is preferred. The cations may be used alone or as a combination of two or more of them.

Particularly preferred among the zeolites is proton-type H-ZSM-5 having MFI structure.

Although the molar ratio of $SiO_2$ to $Al_2O_3$ ($SiO_2/Al_2O_3$) in the crystalline structure of zeolite varies depending on the particular reactor, temperature, and impurities in the materials, the molar ratio is preferably 5 to 2000, more preferably 10 to 500, still more preferably 12 to 70, and particularly preferably 15 to 35. The molar ratios in these ranges can lead to minimization of further secondary reactions (e.g. alkylation) of the generated benzene. Based on the same reason, the crystal size of zeolite is preferably (0.001 to 50) μm× (0.01 to 100) μm. The particle size of zeolite is preferably 0.1 to 50 μm, and more preferably 1 to 20 μm. Also, the nitrogen adsorption specific surface area of zeolite is preferably 10 to 1000 $m^2/g$, and more preferably 100 to 500 $m^2/g$.

Examples of the aromatic compound synthesized from the alcohol having two or more carbon atoms include benzene, toluene, xylene, ethylbenzene, diethylbenzene, and butylbenzene. In particular, in terms of efficient synthesis of aniline or styrene, benzene and ethylbenzene are preferred, and benzene is more preferred. The benzene may be synthesized via toluene or xylene, or via an alkene such as ethylene.

The apparatus for synthesizing the aromatic compound is not particularly limited. For example, an apparatus may be used in which a heating device and a material feeding system are attached to a reaction tube or the like carrying a catalyst. In terms of enhancing the efficiency of conversion into a target product, the apparatus preferably includes a circulation system for subjecting the alcohol to catalysis by the solid acid catalyst to give a reaction product, and circulating the reaction product so that it is further subjected to catalysis by the solid acid catalyst.

The circulation system is preferably a system which is adapted to distill the reaction product to separate a target product, and circulate compounds other than the target product, such as high-boiling reaction products and gaseous reaction products which have not been distilled out, so that they are further subjected to catalysis by the catalyst. Here, in the case where the target product is benzene, a system for cooling the generated benzene to not higher than the melting point (5.5° C.) of benzene to recover benzene is more preferred from the viewpoint of the efficiency of conversion into benzene. Furthermore, the circulation system preferably repeats such a circulation.

In the case of synthesizing the aromatic compound via an alkene, from the viewpoint of high benzene yield and maintenance of long life of the catalyst, the apparatus preferably includes a system including two reaction columns coupled to each other, in which an alcohol is dehydrated to produce an alkene in the first column, and then an aromatic compound is synthesized in the second column.

The method for synthesizing aniline from the aromatic compound is not particularly limited, and conventionally known methods may be employed. For example, mention may be made of a method including reacting benzene with an acid mixture of concentrated nitric acid and concentrated sulfuric acid, and reducing the resulting nitrobenzene by a reduction technique such as Bechamp reduction or catalytic reduction.

Similarly, regarding the method for synthesizing styrene from the aromatic compound, conventionally known methods may be employed. For example, mention may be made of a method including ethylation of benzene by Friedel-Crafts reaction or the like, followed by dehydrogenation of the resulting ethylbenzene with an iron catalyst or the like. The ethylene used in Friedel-Crafts reaction can be produced, for example, by dehydration of bioethanol, and therefore styrene can be produced without petroleum resources.

In the case where ethylbenzene is directly synthesized as the aromatic compound, the ethylbenzene, as it is, is dehydrogenated to synthesize styrene.

The second aspect of the present invention relates to a synthesis system (synthesis method) for synthesizing aniline from a biomass material via phenol.

First, a process of biosynthesis of phenol from a biomass resource by using a microorganism is explained.

The microorganism usable in the second aspect of the present invention is not particularly limited as long as it can utilize a biomass resource to biosynthesize phenol.

For example, in order to biosynthesize phenol, a biomass resource can be utilized by a microorganism obtainable by introducing a gene (tpl gene) (for example, the tpl gene listed in GenBank under accession No. D13714) encoding tyrosine phenol lyase (EC 4.1.99.2), an enzyme catalyzing a reaction to produce phenol from tyrosine, into a microorganism capable of biosynthesizing tyrosine.

It should be noted that tyrosine phenol lyase is a pyridoxal-5'-phosphate-dependent enzyme, and catalyzes a reaction to produce phenol, pyruvic acid, and ammonia from tyrosine. Tyrosine phenol lyase is also known as β-tyrosinase or L-tyrosine phenol lyase.

The microorganism into which the tpl gene is to be introduced is not particularly limited as long as it can biosynthesize tyrosine. Since almost all microorganisms on the earth can biosynthesize tyrosine, any microorganism can be used. Examples thereof include microorganisms belonging to the genus *Escherichia*, the genus *Serratia*, the genus *Bachillus*, the genus *Brevibacterium*, the genus *Corynebacterium*, the genus *Microbacterium*, the genus *Pseudomonas*, the genus *Agrobacterium*, the genus *Alicyclobacillus*, the genus *Anabena*, the genus *Anacystis*, the genus *Arthrobacter*, the genus *Azotobacter*, the genus *Chromatium*, the genus *Erwinia*, the genus *Methylobacterium*, the genus *Phormidium*, the genus *Rhodobacter*, the genus *Rhodopseudomonas*, the genus *Rhodospirillum*, the genus *Scenedesmus*, the genus *Streptomyces*, the genus *Synechoccus*, the genus *Zymomonas*, or the like. Among these examples, microorganisms belonging to the genus *Pseudomonas* are preferred.

In general, microorganisms may die when the concentration of the generated phenol is high. For this reason, the microorganism into which the tpl gene is to be introduced is preferably resistant to organic solvents (especially resistant to aromatic compounds) to prevent the microorganism from dying easily due to phenol. Examples of microorganisms resistant to organic solvents include *Pseudomonas putida* S12. *Pseudomonas putida* S12 has excellent resistance to aromatic compounds, and can therefore be suitably used as the microorganism into which the tpl gene is to be introduced.

The method for introducing the tpl gene into the microorganism is not particularly limited, and a commonly-used method may be performed under generally known conditions. Examples of the method include, but not limited to, a method using calcium ions (Proc. Natl. Acad. Sci., USA, 69, 2110 (1972)), a protoplast method (JP-A S63-248394), an electroporation method (Nucleic Acids Res., 16, 6127 (1988)), a heat shock method, and a particle gun method ("Seibutsu-kagaku jikken-ho (Experimental Methods in Biochemistry) 41, Syokubutsu-Saibo Kogaku Nyumon (Basic Plant Cell Technology)", Sep. 1, 1998, Japan Scientific Societies Press, pp. 255-326).

The culture medium for culturing the microorganism into which the tpl gene has been introduced is not particularly limited as long as it allows growth of the microorganism to be cultured but contains a biomass resource used as a carbon source. Ordinary culture media further containing a nitrogen source, inorganic ions, and optionally an organic nutrient source may be used.

The biomass resource is not particularly limited as long as it contains a sugar. Examples thereof include rice, wheat, honey, fruits, corn, sugar cane, bagasse, kenaf, legumes, straw, wheat straw, rice hulls, thinning residues, waste wood, waste paper, waste pulp, and organic urban waste. Moreover, mention may be made of sugars such as glucose, sucrose, trehalose, fructose, lactose, galactose, xylose, mannitol, sorbitol, xylitol, erythritol, maltose, amylose, cellulose, chitin, and chitosan. Preferred among the examples are sugars.

In the second aspect of the present invention, the biomass resource may be directly used as a carbon source. However, in the case of using biomass resources other than the above sugars or polysaccharides such as cellulose, chitin and chitosan, these biomass resources other than the sugars, and polysaccharides are preferably used after the molecular weight thereof is reduced because, for example, some microorganisms cannot directly utilize them or some have low ability to utilize them. The method for reducing the molecular weight is not particularly limited, and known methods (e.g. steam treatment, hydrolysis, enzymatic degradation) may be used. Monosaccharides and the like can be obtained by reducing the molecular weight of the biomass resource other than the sugars or polysaccharide.

Glucose is particularly preferred among the above biomass resources because it contributes to efficient production of phenol. Examples of usable glucose include those existing naturally as glucose (monosaccharide) and those obtained by reducing the molecular weight of biomass resources by the above-mentioned methods and the like.

Examples of the nitrogen source include inorganic ammonium salts such as ammonium sulfate and ammonium chloride; organic acid ammonium salts such as ammonium fumarate and ammonium citrate; nitrates such as sodium nitrate and potassium nitrate; organic nitrogen compounds such as peptone, yeast extract, meat extract, corn steep liquor and soybean hydrolysate; ammonia gas and ammonia water; and mixtures of these.

Furthermore, an appropriate mixture of nutrient sources used in ordinary culture media, such as inorganic salts, trace metal salts, vitamins and hormones, may also be used.

The culture conditions are not particularly limited. For example, the culture may be performed under aerobic conditions while appropriately controlling the pH in the range of 5 to 8, and the temperature in the range of 20° C. to 60° C. (preferably 20° C. to 35° C.) for about 12 to 480 hours. The culture may be performed by either solid or liquid culture. From the viewpoint of efficiency, liquid culture is more preferred. The liquid culture may be performed by any of batch culture, semi-batch culture, and continuous culture.

By culturing the microorganism, a biomass resource can be utilized to biosynthesize phenol. Phenol may be recovered by extraction from the culture liquid or the phenol accumulated in the microorganism may be extracted.

The phenol accumulated in the culture liquid may be extracted with, for example, an organic solvent. Examples of usable organic solvents include, but not limited to, diethyl ether, octanol, nonanol, dodecanol, benzene, toluene, xylene, and ethyl acetate. Furthermore, the phenol extracted with the organic solvent may be purified by a known purification operation such as chromatography.

The phenol accumulated in the microorganism can be obtained by ultrasonic disruption of the microorganism and then extraction with the organic solvent.

Alternatively, phenol may be recovered by removing water from the culture liquid alone or from both the culture liquid and the microorganism, followed by extraction with an organic solvent such as ethanol, and then purification.

Another method for synthesizing phenol from a biomass resource includes conversion of bioethanol to phenol by using a solid acid catalyst. Examples of the solid acid catalyst include, but not limited to, zeolite catalysts and alumina catalysts. A plurality of catalysts may be used stepwise or simultaneously.

The solid acid catalyst may be ion-exchanged, and may further carry a member selected from the group consisting of metals such as alkali metals, alkaline earth metals, iron, aluminum, gallium, zinc, gadolinium, platinum, vanadium, palladium, niobium, molybdenum, yttrium, rhenium, neodymium, tungsten, lanthanum, copper, titanium, and ruthenium, and compounds of these metals; and phosphorus compounds, boron compounds and the like. Solid acid catalysts carrying a member selected from the group consisting of simple substances of copper, titanium, platinum and ruthenium, and compounds thereof, are preferred.

As the solid acid catalyst, zeolites are particularly preferred, and specific examples thereof include A-type zeolites, L-type zeolites, X-type zeolites, Y-type zeolites, MFI-type zeolites, MWW-type zeolites, β-type zeolites, mordenite, ferrierite, and erionite. Among the zeolites, MFI-type zeolites are preferred, and ZSM-5-type zeolites are particularly preferred. Combination use of a proton-type ZSM-5 catalyst and a ZSM-5 catalyst carrying a rare earth such as gadolinium and rhenium is preferred.

Next, examples of the method for synthesizing aniline from the biosynthesized phenol include methods in which by using various catalysts, the phenol is allowed to react with ammonia gas or a low-molecular amine compound to prepare aniline. Examples of the catalysts include, but not limited to, solid catalysts such as zeolite catalysts, niobium catalysts, titania-zirconia composite oxide catalysts, alumina catalysts and metallosilicate catalysts, and various inorganic acids and organic acids. A plurality of catalysts may be used stepwise or simultaneously.

The solid catalysts may be ion-exchanged, and may further carry a member selected from the group consisting of metals such as alkali metals, alkaline earth metals, iron, copper, aluminum, gallium, zinc, gadolinium, platinum, vanadium, palladium, titanium, niobium, molybdenum, yttrium, rhenium, neodymium, tungsten, and lanthanum, and compounds of these metals; and phosphorus compounds, boron compounds and the like.

As the solid catalysts, zeolites are particularly preferred, and specific examples thereof include A-type zeolites, L-type zeolites, X-type zeolites, Y-type zeolites, MFI-type zeolites, MWW-type zeolites, β-type zeolites, mordenite, ferrierite, and erionite.

Zeolites of MWW-type MCM-22 and of MFI-type are preferred, and these zeolites may carry another catalyst. The MFI-type zeolites are zeolites having MFI (Mobil five) structure, and examples thereof include zeolites having MFI structure such as ZSM-5, ZSM-8, zeta 1, zeta 3, Nu-4, Nu-5, TZ-1, TPZ-1, and TS-1. From the viewpoint of high selectivity and good reaction efficiency, ZSM-5-type zeolites are particularly preferred among the above examples.

Cations occupying the ion-exchangeable cation sites of zeolite are not particularly limited, and examples thereof include hydrogen ion (proton); alkali metal ions such as lithium ion, sodium ion, and potassium ion; alkaline earth metal ions such as magnesium ion, calcium ion, strontium ion, and barium ion; transition metal ions such as iron ion and silver ion; and primary to quaternary ammonium ions. In particular, in terms of achieving high reaction efficiency by enhancement of the surface activity, hydrogen ion (proton) is preferred. The cations may be used alone or as a combination of two or more of them.

Although the molar ratio of $SiO_2$ to $Al_2O_3$ ($SiO_2/Al_2O_3$) in the crystalline structure of zeolite varies depending on the particular reactor, and impurities contained in the materials, the molar ratio is preferably 5 to 2000, and more preferably 5 to 60. The molar ratios in these ranges can lead to minimization of further secondary reactions (e.g. alkylation) of the generated phenol. Based on the same reason, the crystal size of zeolite is preferably (0.001 to 50) μm×(0.01 to 100) μm. The particle size of zeolite is preferably 0.1 to 50 μm, and more preferably 1 to 20 μm. Also, the nitrogen adsorption specific surface area of zeolite is preferably 10 to 1000 $m^2/g$, and more preferably 100 to 500 $m^2/g$.

The reaction of phenol and ammonia catalyzed by the catalyst may be a gas phase reaction or a liquid-phase reaction. Examples of usable reactors include fixed bed reactors, fluidized bed reactors, and moving bed reactors. The reaction temperature is preferably about 200° C. to 600° C. (more preferably 300° C. to 500° C., and still more preferably 350° C. to 450° C.). The reaction may be performed at either normal or increased pressure (preferably at about 5 to 50 atm). Furthermore, the molar ratio of ammonia to phenol is about 1 to 50 (preferably 5 to 30). In the reaction, the reaction system may optionally be diluted with inert gas such as nitrogen, argon, and steam.

Use of the aniline prepared as above contributes to reduction in the amount of petroleum resources used in the production of rubber chemicals for a tire such as antioxidants and vulcanization accelerators, and furthermore it enables production of such rubber chemicals for a tire without using petroleum resources.

Examples of the antioxidants include p-phenylenediamine antioxidants such as N-(1,3-dimethylbutyl)-N'-phenyl-p-phenylenediamine; and quinoline antioxidants such as 2,2,4-trimethyl-1,2-dihydroquinoline polymers.

For example, N-(1,3-dimethylbutyl)-N'-phenyl-p-phenylenediamine can be produced from aniline according to the below-mentioned method. Here, methyl isobutyl ketone to be added to an amine as an intermediate can be synthesized by the following method. Diacetone alcohol, which can be synthesized by, for example, aldol condensation of two molecules of the acetone synthesized by the below-mentioned method, is easily dehydrated to be converted to mesityl oxide. Then, hydrogenation of the mesityl oxide with a palladium catalyst or the like gives methyl isobutyl ketone. According to such a method, antioxidants can be produced without using petroleum resources.

Moreover, 2,2,4-trimethyl-1,2-dihydroquinoline polymers can be synthesized from aniline by feeding acetone any time as needed at a temperature of 140° C. in the presence of an acidic catalyst. Since acetone can be produced by the following method, the polymers can be produced without using petroleum resources.

Acetone required for the synthesis of the antioxidants can be synthesized, for example, as follows: a biomass material is subjected to acetone-butanol fermentation by a microorganism to give a mixed solvent of butanol, acetone and the like, and the mixed solvent is distilled so that acetone is obtained. Examples of the biomass material include cellulose, agricultural products and waste thereof, and sugars, and sugars are particularly preferred. The microorganism for the acetone-butanol fermentation is not particularly limited. Preferred examples of the microorganism include wild type, variants, or recombinants of a member selected from the group consisting of those belonging to the genus *Escherichia*, the genus *Zymomonas*, the genus *Candida*, the genus *Saccharomyces*, the genus *Pichia*, the genus *Streptomyces*, the genus *Bacillus*, the genus *Lactobacillus*, the genus *Coryne*, or the genus *Clostridium*. Microorganisms belonging to the genus *Clostridum* are more preferred, and *Clostridium acetobutylicum*, *Clostridium beijerinckii*, *Clostridium saccharobutylicum*, and *Clostridium saccharoperbutylacetonicum* are particularly preferred.

Moreover, microorganisms containing a gene encoding acetoacetate decarboxylase (EC4.1.1.4), coenzyme A transferase, or thiolase from a microorganism of the genus *Clostridium* may be used.

Acetone may also be obtained by dry distillation of wood to give pyroligneous acid, followed by further fractional distillation or separation by liquid chromatography or the like.

Also, acetone can be synthesized by heating bioethanol at a temperature of 400° C. or higher in the presence of a Zr—Fe catalyst.

Moreover, acetone can be synthesized through the following steps of: subjecting bioethanol derived from a carbohydrate material to a dehydration reaction to synthesize ethylene, synthesizing propylene from the ethylene by a general technique in the petrochemical industry, and subjecting the propylene to a hydration reaction to prepare isopropanol, followed by dehydrogenation.

Furthermore, acetone can be synthesized by pyrolyzing cellulose in a wood material to give acetic acid, neutralizing the acetic acid with calcium hydroxide to give calcium acetate, and then pyrolyzing the calcium acetate. Since acetic acid is generated by oxidation of ethanol during the fermentation in the synthesis of bioethanol, the acetic acid can be utilized to synthesize acetone through the same process as above.

Still furthermore, acetone can be synthesized by subjecting bioethanol derived from a carbohydrate material to a conversion reaction by a ZnO/CaO catalyst or the like.

Examples of the vulcanization accelerators include thiazole vulcanization accelerators such as 2-mercaptobenzothiazole and dibenzothiazyl disulfide; and sulfenamide vulcanization accelerators such as N-cyclohexyl-2-benzothiazylsulfenamide, N,N-dicyclohexyl-2-benzothiazylsulfenamide, and N-tert-butyl-2-benzothiazylsulfenamide.

According to the following synthesis method, 2-mercaptobenzothiazole can be produced from aniline. Here, carbon disulfide can be produced, for example, by reacting mustard oil contained in an amount of about 0.4% in *Brassica juncea*, with hydrogen sulfide to separate the carbon disulfide. According to such a method, vulcanization accelerators can be produced without using petroleum resources. Moreover, oxidation of the thus-produced 2-mercaptobenzothiazole gives dibenzothiazyl disulfide.

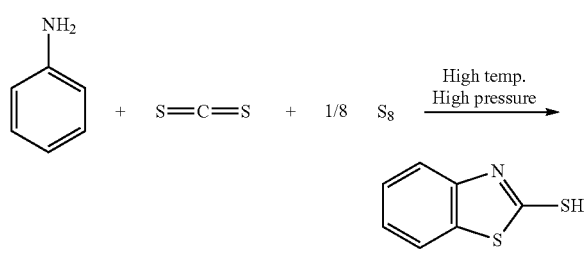

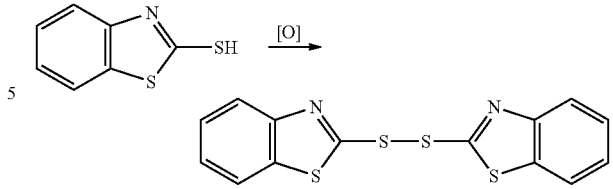

The above-prepared styrene and 1,3-butadiene can be used to produce a synthetic rubber for a tire without using petroleum resources.

Examples of the synthetic rubber for a tire include styrene butadiene rubber (SBR), and butadiene rubber (BR). SBR can be produced by copolymerization of styrene and 1,3-butadiene. BR can be produced by polymerization of 1,3-butadiene. Here, 1,3-butadiene can be produced, for example, by a method of reacting bioethanol at a high temperature in the presence of a solid acid catalyst as mentioned above, such as zeolites, alumina, titanium compounds, sulfate ion-supported zirconia, and $WO_3$-supported zirconia; or a method of oxidizing bioethanol to give acetaldehyde, followed by addition of bioethanol in the presence of a tantalum/silicon dioxide catalyst and then heating. Thus, synthetic rubbers for a tire can be produced without using petroleum resources.

The rubber chemicals for a tire and the synthetic rubbers for a tire obtained as above may be used for rubber compositions for a tire (treads, sidewalls, etc.).

In addition to the above components, the rubber compositions appropriately contain other compounding ingredients usually used in the rubber industry, such as inorganic fillers (e.g. carbon black, silica, clay, aluminum hydroxide, calcium carbonate), silane coupling agents, process oil, softeners, vulcanizing agents, and vulcanization accelerating auxiliaries. The rubber compositions may partially contain ordinary antioxidants, vulcanization accelerators and synthetic rubbers, which are derived from fossil resources such as petroleum.

The rubber compositions may be produced by known methods. For example, the composition can be produced by kneading the components with a rubber kneader such as an open roll mill, a Banbury mixer, and an internal mixer, and vulcanizing the resulting mixture.

The pneumatic tire of the present invention can be produced by a usual method using the rubber composition. Specifically, an unvulcanized rubber composition containing the components as needed is extruded and processed into the shape of a tire component, and then subjected to molding in a usual manner on a tire building machine to form an unvulcanized tire. Thereafter, the unvulcanized tire is subjected to heat and pressure in a vulcanizer to produce a tire.

EXAMPLES

The following description is offered to specifically illustrate the first aspect of the present invention based on examples. The first aspect of the present invention, however, is not limited only to these examples.

(Synthesis of Benzene from Alcohol)

Example 1

Ethyl alcohol for industrial use (petroleum-derived ethanol) prepared by hydration of petroleum-derived ethylene was used as an alcohol material.

Benzene was synthesized from the alcohol by using a flow reactor (see, FIG. 1) provided with a gas introduction pipe 1, an alcohol introduction pipe (material introduction pipe) 2, a reaction tube 3 having an alcohol vapor layer (material vapor layer) 4 and a catalyst layer (reaction layer) 5, a heater (electric furnace) 6 for heating the reaction tube 3, a product trap 7 for collecting a product generated through the catalyst layer 5, and a cooling device 8a. The product trap 7 was cooled to −15° C. with the cooling device 8a.

An amount of 10.0 g of a zeolite catalyst H-ZSM-5 (produced by Tosoh Corporation, 840 HOA, a calcined product of 840 NHA ($SiO_2/Al_2O_3$=40 (molar ratio), nitrogen adsorption specific surface area: 330 m$^2$/g, crystal size: 2 μm×4 μm, particle size: 10 μm)) was placed on a quartz wool provided inside the catalyst layer 5, and nitrogen gas was fed from the gas introduction pipe 1. The feed rate of nitrogen gas in terms of LHSV was set to 1/hr. The reaction tube 3 was warmed by the heater 6 to a predetermined temperature, and then a predetermined amount of petroleum-derived ethanol was fed from the alcohol introduction pipe 2. The reaction conditions were as follows: reaction temperature: 500° C., reaction pressure: normal pressure, feed rate of petroleum-derived ethanol: 1/hr in terms of LHSV, molar ratio of petroleum-derived ethanol to nitrogen (petroleum-derived ethanol/nitrogen): 50/50. The reaction time was two hours. The resulting product was collected in the product trap 7 connected to the reaction tube 3.

The product was analyzed by gas chromatography. PORAPAK P (registered trademark, produced by GL Sciences Inc.) was used as a column filler for analysis of the gas component, and SUPELCOWAX (registered trademark, produced by SUPELCO) was used as a column filler for analysis of other components.

The conversion rate of the petroleum-derived ethanol was 100%. Based on comparison of the number of moles of carbon, the resulting product consisted of benzene (12.0%), toluene (14.2%), xylene (7.6%), and others (66.2%).

Benzene was recovered by distilling the product. The reflux ratio was set to 2, and the steam flow rate was set to 0.2 m/s. With the above ratio of the number of moles produced, the recovery efficiency by distillation was 90%. Accordingly, the total yield of benzene calculated from the equation below was 11%.

Total yield (%)=(number of moles of carbon of benzene produced per unit time)/(number of moles of carbon of ethanol fed per unit time)×recovery efficiency by distillation×100

Example 2

Benzene was synthesized in the same manner as in Example 1. In the synthesis, toluene and xylene as by-products were recovered, and were again allowed to react in the presence of the zeolite catalyst used in Example 1. The total yield of benzene was 17%.

Example 3

Benzene was synthesized in the same manner as in Example 1, except that bioethanol was used instead of the petroleum-derived ethanol. The bioethanol used was derived from corn, and contained about 20% of water, and about 8% of other components such as acetaldehyde. The bioethanol was used after filtration alone without purification by distillation. The total yield of benzene was 13%.

Example 4

Benzene was synthesized in the same manner as in Example 3, except that a zeolite catalyst H-ZSM-5 (produced by Tosoh Corporation, 820 HOA, a calcined product of 820 NHA ($SiO_2/Al_2O_3$=23 (molar ratio), nitrogen adsorption specific surface area: 350 m$^2$/g, crystal size: 0.03 μm×0.1 μm, particle size: 5 μm)) was used instead of the 840 HOA (produced by Tosoh Corporation). The total yield of benzene was 21%.

Example 5

Benzene was synthesized in the same manner as in Example 1, except that a zeolite catalyst H-mordenite (CBV90A ($SiO_2/Al_2O_3$=90), produced by Zeolyst) was used instead of the 840 HOA (produced by Tosoh Corporation). The total yield of benzene was 1%.

Comparative Example 1

Benzene was synthesized in the same manner as in Example 5, except that coal-derived methanol (methanol for industrial use prepared by reacting carbon monoxide (CO) produced by partial oxidation of coals, with hydrogen under a pressure of 50 to 100 atm at a temperature of 240° C. to 260° C. in the presence of a copper oxide/zinc oxide/alumina composite oxide catalyst) was used instead of the petroleum-derived ethanol. The total yield of benzene was 0.5%.

Example 6

Figure 2:
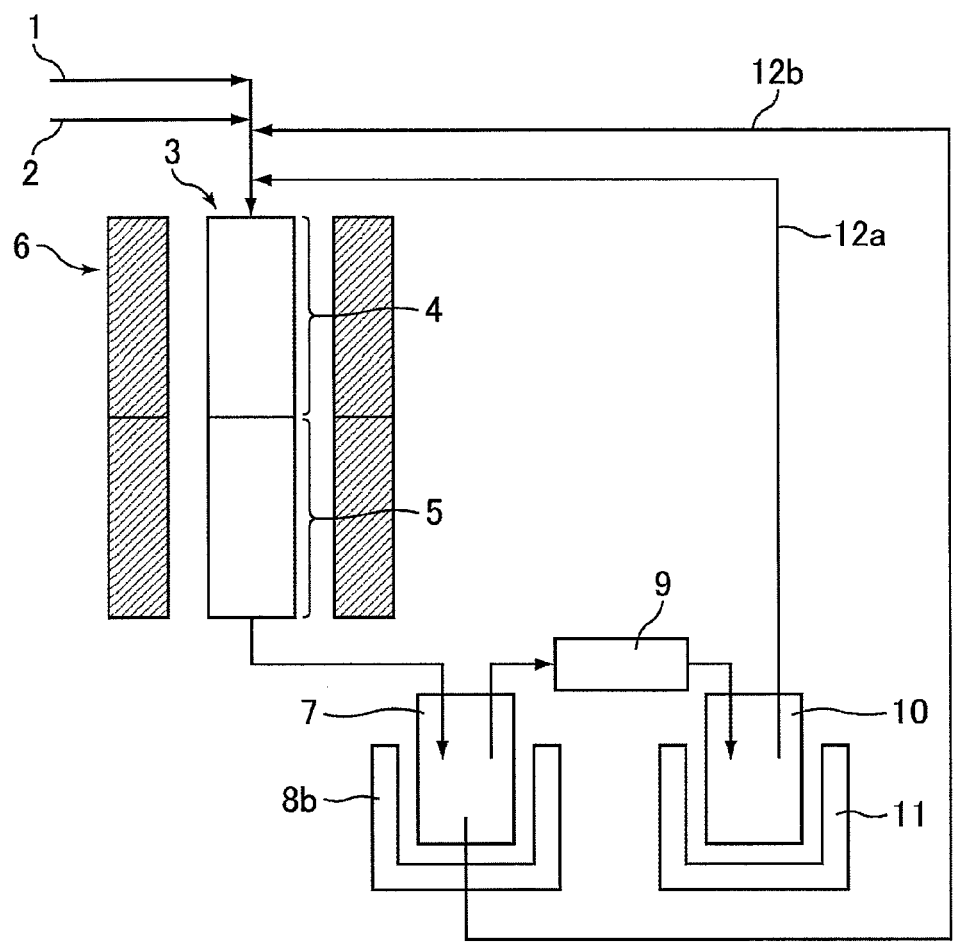
FIG. 2 is a schematic view showing one embodiment of an apparatus (circulation type) for directly synthesizing an aromatic compound from an alcohol.

Benzene was synthesized from petroleum-derived ethanol by using the zeolite catalyst used in Example 4. The synthesis was performed using a system (circulation reactor) (see, FIG. 2) including the apparatus shown in FIG. 1 in which the product trap 7 was attached with a heater 8b, a fractionator (fractioning pipe) 9, a distillate trap (target product trap) 10, and a reactant recirculation lines 12a and 12b. In the system, a reaction mixture obtained by a catalytic reaction was subjected to fractional distillation to separate low-boiling products, and then vaporized components and high-boiling products were continuously supplied to the reaction tube 3. The product trap 7 was heated with the heater 8b so that the inside temperature was 90° C.

A reaction was allowed to proceed under the conditions of Example 4 using the reactor. The reaction product was continuously distilled through the fractioning pipe 9. Subsequently, benzene in the distillate was solidified and recovered in the distillate trap 10 cooled to −15° C. by a cooling device 11. Gaseous products that had not been solidified or liquefied, and high-boiling products that had not been distilled out were allowed to be continuously supplied to the reaction tube 3 through the reactant recirculation lines 12a and 12b.

After feeding petroleum-derived ethanol under the same conditions as in Example 4, the feeding was stopped, and the circulation reaction was maintained for 14 hours under the same heating conditions. The total yield of benzene was 31%.

Example 7

Benzene was synthesized in the same manner as in Example 6, except that bioethanol was used instead of the petroleum-derived ethanol. The total yield of benzene was 39%.

(Discussion of Synthesis Examples of Benzene from Alcohol)

Comparison of Example 1 and Example 2 reveals that the yield of benzene is increased by repetition of the catalytic reaction of the by-products. This is considered to be because toluene and xylene as by-products are converted to benzene by the catalyst. The results demonstrate an advantage achieved by repetition of the catalytic reaction step in this process.

Comparison of Example 3 and Example 4 reveals that a difference in the Si/Al ratio ($SiO_2/Al_2O_3$ ratio) of the zeolite catalyst leads to different reactivity and selectivity. However, the reactivity and selectivity supposedly depend also on the reaction temperature and configuration of the apparatus. Therefore, optimization of the Si/Al ratio according to the reaction apparatus to be used is considered necessary in some cases.

Example 3 reveals that the use of bioethanol that contains by-products mainly consisting of water also allows the reaction in the present invention to proceed. Comparison of the yields of benzene in Example 1 and in Example 3 in terms of the number of moles of carbon while considering the ethanol content shows that the yield in Example 3 in which bioethanol was used was slightly higher than the yield in Example 1.

Comparison of Examples 1, 2, 4 and 7 reveals that the yield of benzene is greatly increased by repeatedly bringing the by-products into contact with the catalyst layer for a plurality of times or in a continuous manner.

Comparison of the yields of benzene in Example 6 and in Example 7 in terms of the number of moles of carbon while considering the ethanol content surprisingly shows that the yield of benzene was higher in Example 7 in which bioethanol was used than in Example 6 in which petroleum-derived ethanol was used. This is supposedly not only because the water contained in bioethanol does not considerably inhibit the reaction, but also because other impurities are converted to benzene, or exhibit their functions to activate the conversion reaction or the catalyst.

(Synthesis of Benzene from Alcohol via Alkene)

Example 8

An aromatic compound was synthesized from an alcohol via an alkene by using an apparatus (see, FIG. 3) provided with an alcohol introduction pipe (material introduction pipe) 21, a heater 22 for vaporizing the introduced alcohol, a dehydration reaction column 23 for dehydration reaction of the alcohol, a cooling device 24 for cooling the product resulting from the dehydration reaction to recover an alkene, a heater 25 for vaporizing the alkene, an aromatic compound synthesis column 26 for synthesizing an aromatic compound from the alkene, and a cooling device 27 for recovering the generated aromatic compound. The dehydration reaction column 23 was filled with 10 g of aluminum oxide (101095100, produced by Merck Ltd.) serving as a catalyst, and heated to 300° C. The aromatic compound synthesis column 26 had the same structure as that of the reaction tube 3 shown in FIG. 1. Petroleum-derived ethanol was used as a material, and the ethanol was fed to the dehydration reaction column 23 under the same feeding conditions as in Example 1. The resulting ethylene was allowed to react in the aromatic compound synthesis column 26. The resulting product was distilled and purified to give benzene in a total yield of 27%.

Example 9

Benzene was synthesized in the same manner as in Example 8, except that bioethanol was used instead of the petroleum-derived ethanol. The total yield of benzene was 36%.

Example 10

Figure 3:
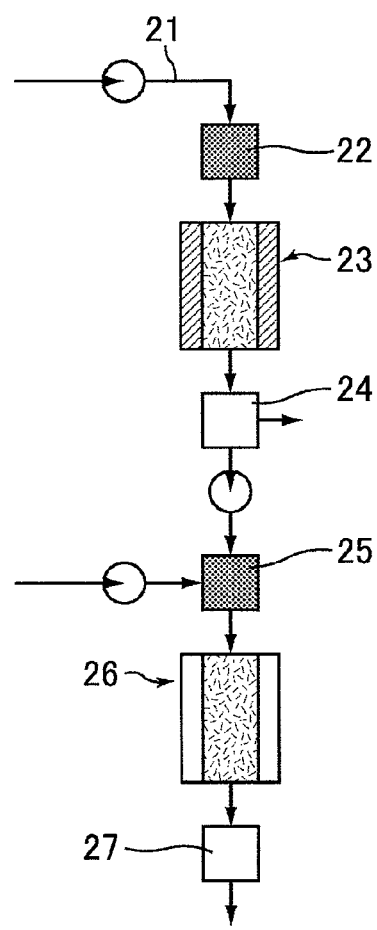
FIG. 3 is a schematic view showing one embodiment of an apparatus for synthesizing an aromatic compound from an alcohol via an alkene.
Figure 4:
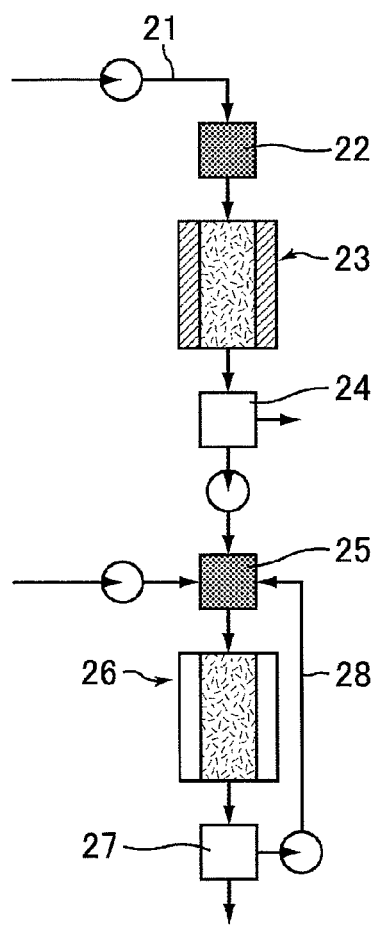
FIG. 4 is a schematic view showing one embodiment of an apparatus (circulation type) for synthesizing an aromatic compound from an alcohol via an alkene.

Benzene was synthesized using an apparatus (see, FIG. 4) having the same structure as that of the apparatus shown in FIG. 3, except that the apparatus further includes a reactant recirculation line 28 for recovering by-products generated in the aromatic compound synthesis column 26. Benzene was synthesized by feeding petroleum-derived ethanol under the same conditions as in Example 8, with the dehydration reaction column 23 and the aromatic compound synthesis column 26 heated to 300° C. and 500° C., respectively. Similarly to Example 6, the circulation reaction time was set to 14 hours. The resulting product was distilled and purified to give benzene. The total yield of benzene was 82%.

Example 11

Benzene was synthesized in the same manner as in Example 10, except that bioethanol was used instead of the petroleum-derived ethanol. The total yield of benzene was 90%.

(Synthesis of Aniline from Benzene)

Aniline was synthesized from the benzene obtained by the above method, according to the following method.

Sulfuric acid was added to a chloroform solution containing the benzene. To the solution was then added nitric acid, and the mixture was heated at a temperature of 50° C. for five hours. After completion of the reaction, the organic layer was neutralized with a 5% aqueous potassium carbonate solution, washed with water, and dried on magnesium sulfate. The solvent was evaporated to give a white solid. The white solid was recrystallized in petroleum-derived ethanol to give nitrobenzene. The obtained nitrobenzene was allowed to react with hydrogen gas at a temperature of 200° C. in the presence of a nickel catalyst so that aniline was obtained.

(Method of Preparing Acetone without using Petroleum Resources)

(Method 1-1 of Preparing Acetone without using Petroleum Resources)

A 300-mL fermenter (DASGIP) was filled with 250 mL of a synthesis medium described by Soni et al. (Soni et al., 1987, Appl. Microbiol. Biotechnol. 27: 1-5), and nitrogen was sparged through the medium for 30 minutes. *Clostridium acetobutylicum* (ATCC824) was inoculated on the resulting medium under anaerobic conditions. The culture temperature was maintained at constant 35° C., and the pH was constantly controlled to 5.5 with a $NH_4OH$ solution. The anaerobic conditions were maintained and the shaking speed was maintained at 300 rpm during the fermentation period. After five days culture, the culture liquid was distilled and subjected to separation by a conventionally known ion-exchange resin method to give acetone.

(Method 1-2 of Preparing Acetone without using Petroleum Resources)

Acetone was obtained through culture and separation in the same manner as in the above preparation method 1-1, except that the strain IFP903 (ATCC39057) was used instead of the strain of *Clostridium acetobutylicum*.

(Method 2 of Preparing Acetone without using Petroleum Resources)

Wood chips were placed in an autoclave provided with a smoke-guiding pipe with a cooling pipe, and were heated to 400° C. to collect pyroligneous acid generated. The precipitated tar was removed from the obtained pyroligneous acid, and the resulting pyroligneous acid was extracted with diethyl ether. The extract was washed with a sodium hydrogen carbonate solution, and then fractional distillation of the washed extract was repeated. Thus, acetone was obtained.

Production Example 1 of Antioxidant from Aniline (Method of Synthesis of Antioxidant TMDQ-1 in Table 1)

To a flask equipped with an acetone introduction device, a distillation device, a thermometer, and a stirrer were added 190 g (2.0 mol) of the aniline obtained above (Synthesis of aniline from benzene) and hydrochloric acid (0.20 mol) as an acidic catalyst, and the mixture was heated to 140° C. Subsequently, 580 g (10 mol) of the acetone obtained above (Method 1-2 of preparing acetone without using petroleum resources) was continuously fed to the reaction system over 6 hours while keeping the temperature at 140° C. Unreacted acetone and aniline that were distilled out were returned to the reaction system as needed. As a result, 180.7 g (yield: about 30%) of polymers of 2,2,4-trimethyl-1,2-dihydroquinoline was obtained. The polymerization degree was 2 to 4. Here, unreacted aniline and 2,2,4-trimethyl-1,2-dihydroquinoline monomer were recovered by reduced-pressure distillation. The unreacted aniline was distilled out at 140° C. By further heating to 190° C., the monomer was distilled out. The amount and yield of the monomer were 19.1 g and 6.9%, respectively.

Production Example 2 of Antioxidant from Aniline (Method of Synthesis of Antioxidant 6PPD-1 in Table 1)

Two molecules of the acetone synthesized above (Method 1-2 of preparing acetone without using petroleum resources) were subjected to an aldol condensation reaction to synthesize diacetone alcohol. The diacetone alcohol was then easily dehydrated to be converted to mesityl oxide. The mesityl oxide was hydrogenated with a palladium catalyst to synthesize methyl isobutyl ketone.

The following reaction was performed using the biomass-derived aniline obtained by the above method and nitrobenzene generated in that process. Meanwhile, nitrobenzene may be synthesized by oxidation of a part of the biomass-derived aniline according to a known method.

An amount of 187 g of a 25% aqueous tetramethylammonium hydroxide solution (TMAOH) was concentrated by distillation at a temperature of 55° C. under a pressure of 75 mbar to give a 35% solution. After addition of the biomass-derived aniline (269 mL) to the solution, the aniline/water azeotrope was evaporated at a temperature of 75° C. under a pressure of 75 mbar until the molar ratio of water/base reached about 4:1. Subsequently, 60 g of the nitrobenzene was added and the resulting mixed solution was further stirred for four hours, while distillation of the water/aniline azeotrope was continued. To the crude mixed solution were added 2.2 g of a Pt/C catalyst (5% Pt) and 120 mL of water. Next, at a temperature of 80° C., the pressure was increased to the maximum of 15 bar with hydrogen, and then the reaction mixture was stirred until no further absorption of hydrogen was found. To the resulting mixture was added 100 mL of toluene, and the catalyst was removed by filtration, followed by separation of the mixture into an organic phase and a water phase with a separatory funnel. Then, purification of the organic phase by fractional distillation gave 4-aminodiphenylamine in a yield of 91%.

An amount of 129.3 g of the 4-aminodiphenylamine, 120.2 g of methyl isobutyl ketone synthesized above, 0.77 g of a platinum catalyst (5% Pt on carbon sulfide powder (hydrous product), water content: 55.26% by mass, produced by N.E. Chemcat Corporation), and 0.65 g of activated carbon (Taiko activated carbon S-type, produced by Futamura Chemical Co., Ltd.) were introduced into a stirring autoclave and exposed to a hydrogen atmosphere. Then, the inside temperature of the autoclave was raised from room temperature to 150° C. over about one hour. Subsequently, the hydrogen pressure was increased to 30 kgf/cm$^2$ (2.94 MPa), and a reaction was allowed to proceed at the same temperature and the same pressure while feeding the consumed amount of hydrogen.

After two hours from the start of increasing the hydrogen pressure, hydrogen was released from the autoclave to decrease the pressure to normal pressure, while the reaction solution was cooled to room temperature. The reaction solution was filtrated to remove the catalyst and the activated carbon. The resulting reaction product was subjected to separation by high performance liquid chromatography to give 4-(1,3-dimethylbutylamino)diphenylamine (antioxidant 6PPD-1) in a yield of 99.4%.

(Method of Preparing Carbon Disulfide without using Petroleum Resources)

Carbon disulfide was obtained by reacting mustard oil contained in an amount of about 0.4% in *Brassica juncea*, with hydrogen sulfide, or by heating charcoal and sulfur at a temperature of 900° C.

Production Example 1 of Vulcanization Accelerator MBT from Aniline (Method of Synthesis of Vulcanization Accelerator MBT-1 in Table 1)

An amount of 93 g (1.0 mol) of the aniline obtained in the above Production Example, 80 g (1.1 mol) of the carbon disulfide obtained above (Method of preparing carbon disulfide without using petroleum resources), and 16 g (1.0 mol) of sulfur were introduced into a 300-mL pressurized reactor, and subjected to a reaction for two hours at a temperature of 250° C. under a pressure of 10 MPa, followed by cooling to 180° C. Thus, a crude product of 2-mercaptobenzothiazole was obtained in an amount of 130 g (yield: 87%). Moreover, the obtained crude product of 2-mercaptobenzothiazole (purity: 79%) was dissolved in isopropanol at the boiling temperature in an inert gas atmosphere of nitrogen. The resulting mixture was left at room temperature to cool. A precipitated product was separated by filtration, washed with isopropanol, and dried. Thus, a light yellow product (2-mercaptobenzothiazole with high purity (melting point: 180.1° C. to 181.1° C., purity: 98.1%)) was obtained.

Production Example 1 of Vulcanization Accelerator CBS from Aniline (Method of Synthesis of Vulcanization Accelerator CBS-1 in Table 1)

The crude product of 2-mercaptobenzothiazole obtained above was dissolved in an aqueous sodium hydroxide solution to prepare a 20% aqueous solution of a sodium salt of mercaptobenzothiazole. To the solution was added an equivalent molar amount of cyclohexylamine. The mixed solution was further mixed with 100 mL of methanol at a temperature of 40° C. A 13% solution of sodium hypochlorite was allowed to act on the resulting mixture, in an amount of 1.2 times the molar amount of the sodium salt of mercaptobenzothiazole, followed by stirring for one hour. After the reaction, water and the organic solvent were removed so that an oil of N-cyclohexyl-benzothiazolylsulfenamide was obtained (yield: 93%).

(Synthesis of Styrene from Benzene)

Benzene was allowed to react with the ethylene obtained by a dehydration reaction of bioethanol in Example 9 or 11, in the presence of aluminum chloride under the following conditions: reaction temperature of 320° C. and benzene/ethylene (molar ratio) of 10 to give ethylbenzene. The obtained ethylbenzene was dehydrogenized in the presence of an iron catalyst to give styrene.

(Method of Preparing 1,3-Butadiene without using Petroleum Resources)

Bioethanol was oxidized to be converted to acetaldehyde, and then bioethanol was added thereto and heated in the presence of a tantalum/silicon dioxide catalyst to give 1,3-butadiene. Alternatively, 1,3-butadiene can be obtained in a small amount in the case where bioethanol is subjected to a dehydration reaction in Example 9 or 11. Thus, this 1,3-butadiene, after separation, may also be used.

(Synthesis of SBR)

Using the styrene and 1,3-butadiene obtained in the above synthesis examples, SBR was polymerized according to the method below.

(Synthesis Example of Solution Polymerized SBR (Method of Synthesis of S-SBR-1 in Table 1))

The inside of a stainless steel polymerization reactor having an internal volume of 20 L was washed and dried, and then the inside air was replaced with dry nitrogen. Hexane (10.2 kg, specific gravity: 0.68 g/cm$^3$), the 1,3-butadiene (547 g) obtained above (Method of preparing 1-3 butadiene without using petroleum resources), the styrene (173 g) obtained above (Synthesis of styrene from benzene), tetrahydrofuran (6.1 mL), and ethylene glycol diethyl ether (5.0 mL) were introduced into the polymerization reactor. Subsequently, n-butyllithium (13.1 mmol) was introduced as an n-hexane solution to start polymerization.

The 1,3-butadiene was copolymerized with the styrene for three hours at a stirring rate of 130 rpm and at a temperature inside the polymerization reactor of 65° C. while continuously feeding the monomers into the polymerization reactor. During the whole polymerization process, 821 g of 1,3-butadiene and 259 g of styrene were fed.

Next, 20 mL of a hexane solution containing 0.54 mL of methanol was added to the polymer solution, and the resulting polymer solution was further stirred for five minutes.

To the polymer solution was added 13.1 mmol of 3-(N,N-dimethylaminopropyl)-trimethoxysilane (produced by AZmax). Then, a solution-polymerized SBR (S-SBR-1) was recovered from the polymer solution by steam stripping.

(Synthesis Example of Emulsion Polymerized SBR (Method of Synthesis of E-SBR-1 in Table 1))

Water (2000 g), a rosin acid soap (45 g, produced by Harima Chemicals, Inc.), a fatty acid soap (1.5 g, produced by Wako Pure Chemical Industries, Ltd.), sodium phosphate (8 g, produced by Wako Pure Chemical Industries, Ltd.), the styrene (250 g) obtained above (Synthesis of styrene from benzene), the 1,3-butadiene (750 g) obtained above (Method of preparing 1-3 butadiene without using petroleum resources), and tert-dodecyl mercaptan (2 g, produced by Wako Pure Chemical Industries, Ltd.) were charged in a pressure-resistant reactor equipped with a stirrer. The temperature of the reactor was set to 5° C. To the reactor were added an aqueous solution containing para-menthane hydroperoxide (1 g, produced by NOF corporation) and sodium formaldehyde sulfoxylate (1.5 g, produced by Wako Pure Chemical Industries, Ltd.), and an aqueous solution containing sodium ethylenediaminetetraacetate (0.7 g, produced by Wako Pure Chemical Industries, Ltd.) and ferric sulfate (0.5 g, produced by Wako Pure Chemical Industries, Ltd.) to start polymerization. After five hours from the start of polymerization, N,N'-dimethyldithiocarbamate (2 g, produced by Wako Pure Chemical Industries, Ltd.) was added to stop the reaction. Thus, a latex was obtained.

Unreacted monomers were removed from the obtained latex by steam distillation. Thereafter, the resulting latex was added to an alcohol, and adjusted to the pH of 3 to 5 with a saturated aqueous sodium chloride solution or formic acid for coagulation to give a polymer crumb. The polymer was dried in a vacuum oven at a temperature of 40° C. so that a solid rubber (emulsion-polymerized SBR (E-SBR-1)) was obtained.

(Synthesis Example of BR)

(Method of Synthesis of BR-1 in Table 1)

The 1,3-butadiene obtained above (Method of preparing 1,3-butadiene without using petroleum resources) was used to polymerize BR (BR-1 in Table 1) according to the following method.

The air inside a reactor (3 L-pressure-resistant stainless steel vessel) was replaced with nitrogen. While maintaining the nitrogen atmosphere, 1800 mL of cyclohexane, 150 g of the 1,3-butadiene obtained above (Method of preparing 1,3-butadiene without using petroleum resources), and 1.5 mL of THF (tetrahydrofuran) were introduced into the vessel, and stirring was started. Next, the temperature inside the vessel was raised to 40° C., and 1 mL of a butyllithium solution was introduced thereinto to start polymerization. After stirring for three hours, 1 mL of a silane solution (1) (a mixed solution of bis(dimethylamino)methylvinylsilane (3 mL) and anhydrous cyclohexane (7.5 mL), produced by Shin-Etsu Chemical Co., Ltd.), and 1.49 mmol of bis(dimethylamino)methylvinylsilane were added and stirred for 15 minutes. An amount of 0.5 mL of IPA (isopropyl alcohol) and 1 mL of a BHT (3,5-dibutyl-4-hydroxytoluene) solution were added to the polymer solution, and further stirred for five minutes. Next, the resulting polymer solution was added to 3 L of methanol to obtain a coagulated polymer, followed by overnight air-drying and then 24-hour drying under reduced pressure. Thus, a polymer (BR-1 in Table 1) was obtained in a yield of 96%. An analysis found that the obtained polymer had an Mw of 26.2×10$^4$, and Mw/Mn of 1.29. The polymer had a vinyl bond content of 11.4 mol % of the conjugated diene unit content (100 mol %).

In this polymer, the content of structural units represented by the following formula (I) calculated from the introduction amount was 0.01 mmol per g of the polymer. The content of conjugated diene structural units in the diene copolymer was 98.4% by mass.

(I)

(in the formula, $X^1$, $X^2$, and $X^3$ each independently represent a group represented by the following formula (Ia), a hydroxyl group, a hydrocarbyl group, or a substituted hydrocarbyl group, and at least one of $X^1$, $X^2$, and $X^3$ is a group represented by the formula (Ia) or a hydroxyl group.)

(Ia)

(in the formula, $R^1$ and $R^2$ each independently represent a C1-C6 hydrocarbyl group, a C1-C6 substituted hydrocarbyl group, a silyl group, or a substituted silyl group, and $R^1$ and $R^2$ may be bound together to form a ring structure with the nitrogen atom.)

(Method of Synthesis of BR-2 in Table 1)

For comparison, an ordinary fossil resource-derived 1,3-butadiene was used to polymerize BR (BR-2 in Table 1) according to the following method.

The air inside a reactor (3 L-pressure-resistant stainless steel vessel) was replaced with nitrogen. While maintaining the nitrogen atmosphere, 1800 mL of cyclohexane, 150 g of fossil resource-derived 1,3-butadiene (produced by Takachiho Chemical Industrial Co., Ltd.), and 1.5 mL of THF were introduced into the vessel, and stirring was started. Next, the temperature inside the vessel was raised to 40° C., and 1 mL of a butyllithium solution was introduced thereinto to start polymerization. After stirring for three hours, 1 mL of the silane solution (1) and 1.49 mmol of bis(dimethylamino)methylvinylsilane were added and stirred for 15 minutes. An amount of 0.5 mL of IPA and 1 mL of a BHT solution were added to the polymer solution, and further stirred for five minutes. The resulting polymer solution was added to 3 L of methanol to obtain a coagulated polymer, followed by overnight air-drying and then 24-hour drying under reduced pressure. Thus, a polymer (BR-2 in Table 1) was obtained in a yield of 96%. An analysis found that the obtained polymer had an Mw of $26.1 \times 10^4$, and Mw/Mn of 1.30. The polymer had a vinyl bond content of 11.3 mol % of the conjugated diene unit content (100 mol %).

In this polymer, the content of structural units represented by the formula (I) calculated from the introduction amount was 0.01 mmol per g of the polymer. The content of conjugated diene structural units in the diene copolymer was 98.4% by mass.

(Preparation of Rubber Composition for Tread)

Chemical agents each in an amount shown in Process 1 in Table 1 were introduced into a Banbury mixer and kneaded for five minutes to raise the outlet temperature to about 150° C. Thereafter, sulfur and vulcanization accelerators each in an amount shown in Process 2 were added to the kneaded mixture obtained in Process 1, and then kneaded with the Banbury mixer for about three minutes to adjust the outlet temperature to 100° C. Thus, an unvulcanized rubber composition was obtained. The resulting unvulcanized rubber composition was molded into a tread shape, assembled with other tire components and then vulcanized for 20 minutes at a temperature of 170° C. Thus, a test tire was produced.

Furthermore, each unvulcanized rubber composition was vulcanized for 20 minutes at a temperature of 170° C. to prepare a vulcanized rubber sheet.

The chemical agents used above were as follows.

S-SBR-1: synthesized by the above method (terminally modified with a compound represented by the following formula (II), bound styrene content: 25% by mass, vinyl content: 59% by mass)

$$R^3-\underset{\underset{R^5}{|}}{\overset{\overset{R^4}{|}}{Si}}-(CH_2)_n-N\diagup^{R^6}_{\diagdown R^7} \quad (II)$$

(in the formula, $R^3$, $R^4$, $R^5$=—$OCH_3$; $R^6$, $R^7$=—$CH_3$; and n=3)

S-SBR-2: SE0190, produced by Sumitomo Chemical Co., Ltd., (terminally modified with a compound represented by the above formula (II), bound styrene content: 25% by mass, vinyl content: 59% by mass)

E-SBR-1: synthesized by the above method

E-SBR-2: SBR1502, produced by JSR Corporation

BR-1: synthesized by the above method

BR-2: synthesized by the above method

NR: RSS #3

Silica: Ultrasil VN2 (BET specific surface area: 125 $m^2$/g), produced by Degussa Carbon black: Niteron #55S (carbon black made from coal-derived heavy oil, $N_2SA$: $28 \times 10^3$ $m^2$/kg), produced by Nippon Steel Chemical Carbon Co., Ltd.

Silane coupling agent: Si69, produced by Degussa

Mineral oil: PS-32, produced by Idemitsu Kosan Co., Ltd.

Stearic acid: Kiri, produced by NOF Corporation

Zinc oxide: zinc oxide #2, produced by Mitsui Mining & Smelting Co., Ltd.

Antioxidant 6PPD-1: synthesized by the above method

Antioxidant 6PPD-2: Nocrac 6C, produced by Ouchi Shinko Chemical Industrial Co., Ltd.

Antioxidant TMDQ-1: synthesized by the above method

Antioxidant TMDQ-2: Nocrac 224, produced by Ouchi Shinko Chemical Industrial Co., Ltd.

Wax: SUNNOC Wax, produced by Ouchi Shinko Chemical Industrial Co., Ltd.

Sulfur: sulfur powder, produced by Tsurumi Chemical Industry Co., Ltd.

Vulcanization accelerator CBS-1: synthesized by the above method

Vulcanization accelerator CBS-2: Nocceler CZ, produced by Ouchi Shinko Chemical Industrial Co., Ltd.

Vulcanization accelerator MBT-1: synthesized by the above method

Vulcanization accelerator MBT-2: Nocceler M, produced by Ouchi Shinko Chemical Industrial Co., Ltd.

The following evaluations were made using the thus obtained unvulcanized rubber compositions, vulcanized rubber sheets, and test tires. Table 1 shows the test results.

(Vulcanization Test)

The unvulcanized rubber composition was exposed to a low amplitude (1° in the test) sinusoidal vibration which did not break the composition, by using a W-type curelastometer (produced by JSR Corporation) according to "Die vulcanization test method A" of "Vulcanization test with oscillating curemeters" in JIS K 6300-2. The torque transferred from the test sample to the upper die was measured during the transition from unvulcanized state to over-vulcanized state so that a vulcanization curve of the unvulcanized rubber composition at a temperature of 170° C. was obtained.

(1) Torque Rise

The torque rise was calculated by subtracting the minimum torque (ML) from the maximum torque (MH). The torque rise of each composition was shown as an index relative to the torque rise of the reference composition (Comparative Example) regarded as 100. The index was used as barometer of crosslinking efficiency. A larger index which indicates higher crosslinking efficiency is favorable.

(2) Cure Time

The tc (95) (95% torque rise point: t95) (min) serving as an indicator of the optimum cure time was calculated. Similarly to the item (1), the tc of each composition was shown as an index relative to the tc of the reference composition (Comparative Example) regarded as 100. A smaller index indicates a higher curing rate.

(Breaking Energy Index)

According to JIS K 6251 "Rubber, vulcanized or thermoplastic—Determination of tensile stress-strain properties", the tensile strength and elongation at break of each vulcanized rubber sheet were measured. The breaking energy was then calculated from the formula: (tensile strength×elongation at break)/2, and furthermore the breaking energy index was calculated from the equation below. A larger breaking energy index indicates better mechanical strength.

(Breaking energy index)=(Breaking energy of each composition)/(Breaking energy of reference composition (Comparative Example))×100

(Abrasion Resistance Test (Abrasion Test))

The produced set of test tires were mounted on a car, and the decrease in the depth of tire grooves after the car had run 8000 km in an urban area was measured. The running distance that decreased the depth of tire grooves by 1 mm was calculated. Further, based on the following equation, the decrease in the depth of tire grooves for each composition was expressed as an abrasion resistance index relative to the abrasion resistance index of a reference comparative example regarded as 100. A larger abrasion resistance index indicates better abrasion resistance.

(Abrasion resistance index)=(Running distance that decreased the groove depth by 1 mm for each composition)/(Running distance that decreased the groove depth by 1 mm for reference composition (Comparative Example))×100

(Rolling Resistance Test)

A vulcanized rubber sheet having a size of 2 mm×130 mm×130 mm was prepared, and a test sample was cut out from the vulcanized rubber sheet. The tan δ of the test sample of each composition was measured using a viscoelastic spectrometer VES (produced by Iwamoto Seisakusho Co., Ltd.) under the following conditions: temperature of 50° C.; initial strain of 10%; dynamic strain of 2%; and frequency of 10 Hz. Based on the equation below, the rolling resistance property was expressed as a rolling resistance index relative to the rolling resistance index of a reference comparative example regarded as 100. A smaller index indicates lower rolling resistance and better fuel economy.

(Rolling resistance index)=(tan δ of each composition)/(tan δ of reference composition (Comparative Example))×100

(Wet Grip Performance)

The grip performance was evaluated based on the braking performance results obtained by the anti-lock braking system (ABS) evaluation test. More specifically, the produced set of test tires were mounted on a 1800 cc-class passenger car equipped with ABS, and the car was driven on an asphalt road surface (road surface condition: wet, skid number: about 50). Then, the brake was stepped on when the speed was 100 km/h, and the deceleration until the car stopped was calculated. The deceleration herein refers to a distance required for the passenger car to stop.

Further, based on the following equation, the deceleration for the tires of each composition was expressed as a wet grip performance index relative to the wet grip performance index of the reference composition (Comparative Example) regarded as 100. A larger wet grip performance index indicates better braking performance and therefore better wet grip performance.

(Wet grip performance index)=(Deceleration for reference composition (Comparative Example))/(Deceleration for each composition)×100

(Dry Grip Performance)

The produced set of test tires were mounted on a passenger car, and the car was driven on a dry asphalt road surface in a test course. The properties of the tires including steering response, rigidity and grip were evaluated based on sensory evaluation by a driver. The results were expressed as an index relative to the results of the reference composition (Comparative Example) regarded as 100. A larger index indicates better performance with better dry grip performance and handling stability.

TABLE 1

|  |  |  | Example | Comparative Example |
|---|---|---|---|---|
| Composition (parts by mass) | Process 1 | S-SBR-1 | 30 |  |
|  |  | S-SBR-2 |  | 30 |
|  |  | E-SBR-1 | 20 |  |
|  |  | E-SBR-2 |  | 20 |
|  |  | BR-1 | 30 |  |
|  |  | BR-2 |  | 30 |
|  |  | NR | 20 | 20 |
|  |  | Silica | 75 | 75 |
|  |  | Carbon black | 5 | 5 |
|  |  | Silane coupling agent | 6 | 6 |
|  |  | Mineral oil | 10 | 10 |
|  |  | Stearic acid | 2 | 2 |
|  |  | Zinc oxide | 3 | 3 |
|  |  | Antioxidant 6PPD-1 | 1.5 |  |
|  |  | Antioxidant 6PPD-2 |  | 1.5 |
|  |  | Antioxidant TMDQ-1 | 0.5 |  |
|  |  | Antioxidant TMDQ-2 |  | 0.5 |
|  |  | Wax | 1.5 | 1.5 |
|  | Process 2 | Sulfur | 1.5 | 1.5 |
|  |  | Vulcanization accelerator CBS-1 | 1.5 |  |
|  |  | Vulcanization accelerator CBS-2 |  | 1.5 |
|  |  | Vulcanization accelerator MBT-1 | 0.2 |  |
|  |  | Vulcanization accelerator MBT-2 |  | 0.2 |
| Evaluations |  | Torque rise | 101 | 100 |
|  |  | Cure time | 99 | 100 |
|  |  | Breaking energy index | 100 | 100 |

TABLE 1-continued

|  | Example | Comparative Example |
|---|---|---|
| Abrasion resistnace index | 101 | 100 |
| Rolling resistance index | 99 | 100 |
| Wet grip performance index | 101 | 100 |
| Dry grip performance index | 100 | 100 |

The rubber properties including vulcanization properties and breaking energy index, and the tire properties including abrasion resistance, rolling resistance property, and wet/dry grip performance in Example were all equal to those in Comparative Example in which conventional vulcanization accelerators, antioxidants, and various synthetic rubbers that were synthesized from fossil resources were used. This demonstrated that the Example makes it possible to cope with depletion of fossil resources without any practical problems.

The following description is offered to specifically illustrate the second aspect of the present invention based on examples. The second aspect of the present invention, however, is not limited only to these examples.

(Synthesis 1 of Phenol from Biomass Material (using Microorganism))

(Preparation of Transformant)

A tpl gene was amplified from genomic DNA of *Pantoea agglomerans* AJ2985 as a template DNA with primers 5'-GCGGTACCATGAACTATCCTGCCGAGCC-3' (forward) (SEQ ID NO: 1) and 5'-GCGGCCGCT-TAAATAAAGTCAAAACGCGC-3' (reverse) (SEQ ID NO: 2) by PCR. The primers herein were designed to contain the sequences GGTACC and CGGCCG, respectively, corresponding to restriction enzymes KpnI and NotI, respectively, based on the sequence of the tpl gene listed in GenBank under accession No. D13714. The amplified tpl gene was confirmed to have no problem in its sequence by a known method.

The amplified tpl gene was incorporated into a plasmid pTn-1, which contained a salicylate-inducible NagR/pNa-gAa promoter and had ampicillin resistance and gentamicin resistance, by using the restriction enzymes KpnI and NotI, so that pNW1 was obtained.

Next, the obtained pNW1 was incorporated into *Pseudomonas putida* S12 (ATCC700801), an organic solvent tolerant bacterium, by a known method, so that a transformant was obtained.

(Semi-Batch Culture)

Next, the obtained transformant was cultured under the following conditions to biosynthesize phenol from glucose. A BioFlo IIc fermentor (produced by New Brunswick Scientific) having an internal volume of 2.5 L was used for the culture. During the culture, oxygen was fed to a headspace of the fermentor at a rate of 300 mL/min, and the fed oxygen was mixed into the medium by rotating an impeller at the bottom of the fennentor. During the culture, the pH was maintained at 7.0 using 4 M KOH. Furthermore, the dissolved oxygen tension was maintained at about 20% saturation by controlling the rotation rate of the impeller. The initial amount of the culture liquid at the start of culture was set to 1.5 L. The absorbance at 600 nm ($OD_{600}$) of the culture liquid was periodically measured. Feeding of a feed liquid was started when no more change was observed in the $OD_{600}$. The feed rate of the feed liquid was set to 4 mL/h when the cell dry weight (CDW) was less than 3 g/L, 9 mL/h when the CDW was 3 to 4.5 g/L, and 20 mL/h when the CDW exceeded 4.5 g/L. The culture was performed at a temperature of 30° C.

The medium composition at the start of culture, and the composition of the feed liquid are as follows.

<Medium Composition at the Start of Culture (The Following Amounts are Per Liter.)>

30 mmol $K_2HPO_4$, 20.5 mmol $NaH_2PO_4$, 25 mmol D-glucose, 15 mmol $NH_4Cl$, 1.4 mmol $Na_2SO_4$, 1.5 mmol $MgCl_2$, 0.5 g yeast extract, 10 ml trace solution 1, 10 mg gentamicin, 0.1 mmol salicylic acid <Composition of Feed Liquid (The Following Amounts are Per Liter.)>

750 mmol D-glucose, 225 mmol $NH_4Cl$, 21 mmol $Na_2SO_4$, 7.4 mmol $MgCl_2$, 13 mmol $CaCl_2$, 0.5 g yeast extract, 100 ml trace solution 2, 10 mg gentamicin, 1 mmol salicylic acid <Composition of Trace Solution 1 (The Following Amounts are Per Liter.)>

4 g EDTA, 0.2 g $ZnSO_4.7H_2O$, 0.1 g $CaCl_2.2H_2O$, 1.5 g $FeSO_4.7H_2O$, 0.02 g $Na_2MoO_4.2H_2O$, 0.2 g $CuSO_4.5H_2O$, 0.04 g $CoCl_2.6H_2O$, 0.1 g $MnCl_2.4H_2O$

<Composition of Trace Solution 2 (The Following Amounts are Per Liter.)>

4 g EDTA, 0.2 g $ZnSO_4.7H_2O$, 0.1 g $CaCl_2.2H_2O$, 6.5 g $FeSO_4.7H_2O$, 0.02 g $Na_2MoO_4.2H_2O$, 0.2 g $CuSO_4.5H_2O$, 0.04 g $CoCl_2.6H_2O$, 0.1 g $MnCl_2.4H_2O$, 0.024 g $H_3BO_3$, 0.02 g $NiCl.6H_2O$

After 25 hours culture, diethyl ether was added to the culture liquid, followed by two times of extraction. The resulting crude extract was concentrated by an evaporator, and then purified by flash chromatography with a column filled with silica gel 60 to give phenol. The phenol was identified by NMR and IR.

(Synthesis 2-1 of Phenol from Biomass Material (using Catalyst))

Copper acetate and $NH_4$-ZSM-5 (produced by Tosoh Corporation, 820 NHA, $SiO_2/Al_2O_3$=23 (molar ratio), nitrogen adsorption specific surface area: 350 m$^2$/g, crystal size: 0.03 μm×0.1 μm, particle size: 5 μm) were used as starting materials to prepare a ZSM-5 catalyst carrying Cu. Ammonia water was added to an aqueous copper acetate solution to adjust the pH to 11 so that copper ions in the solution formed a copper ammine complex $[Cu(NH_3)_4]^{2+}$. To the resulting solution was added $NH_4$-ZSM-5. The mixture was stirred for 24 hours with heating at 60° C. so that the $NH_4$-ZSM-5 was subjected to ion exchange with copper ions, followed by filtration, washing, and drying at 100° C. for 24 hours. The dried product was calcined at 500° C. for one hour under air flow of 1 L/min to give a catalyst. The amount of copper carried by the prepared catalyst was controlled by changing the concentration of the solution used for ion exchange. As a result of an atomic absorption spectroscopy assay, the amount of Cu carried by the prepared catalyst was Cu/Al=0.13 to 1.67 (Cu: 0.54 to 6.83 wt %).

Two quartz tubes each having an inner diameter of 32 mm were connected to each other. The tubes were packed with 10.0 g of a zeolite catalyst H-ZSM-5 (produced by Tosoh Corporation, 820 HOA, a calcined product of 820 NHA ($SiO_2/Al_2O_3$=23)) and 10.0 g of the Cu/ZSM-5 synthesized by the above method, respectively, on quartz wool in the central region of each tube. Nitrogen gas was fed from the catalyst column not carrying Cu. The feed rate of nitrogen gas in terms of LHSV was set to 1/hr. The quarts tubes were placed in an electric furnace, and the temperature was raised to a predetermined temperature. Thereafter, a predetermined amount of bioethanol (produced by BRAZIL-JAPAN ETHANOL Co., Ltd.) purified by distillation was fed. Here, the reaction conditions were as follows: reaction temperature: 450° C., reaction pressure: normal pressure, feed rate of bioethanol in terms of LHSV: 1/hr, molar ratio of bioethanol to nitrogen (bioethanol/nitrogen): 50/50.

A reaction mixture obtained through continuous feeding of bioethanol was distilled, followed by separation by high performance liquid chromatography. Thus, 5 g of pure phenol was obtained.

(Synthesis 2-2 of Phenol from Biomass Material)

An amount of 20 g of phenol was obtained in the same manner as in Synthesis 2-1, except that Re/ZSM-5 modified to carry methyltrioxorhenium by the CVD method was used instead of the Cu/ZSM-5.

(Synthesis 2-3 of Phenol from Biomass Material)

An amount of 0.1642 g (627 µmol) of titanyl bis(acetylacetonate) ($TiO(acac)_2$) was dissolved in 40 mL of methylene chloride. To the solution was added 0.950 g of H-ZSM-5 (produced by Tosoh Corporation, 840 HOA, a calcined product of 840 NHA ($SiO_2/Al_2O_3$=40 (molar ratio), nitrogen adsorption specific surface area: 330 m²/g, crystal size: 2 µm×4 µm, particle size: 10 µm)), and the mixture was stirred under heating at a temperature of 40° C. to remove methylene chloride. After sufficient drying, the dried product was calcined in a muffle furnace under air flow at a temperature of 150° C. for two hours and then at a temperature of 600° C. for four hours. Thus, 1.00 g of a catalyst (TiOx/H-ZSM-5) was prepared. The amount of titanium carried by the prepared catalyst in terms of titanium oxide ($TiO_2$) was 5.0% by mass.

An amount of 8 g of phenol was then obtained in the same manner as in the synthesis example 2-1, except that the TiOx/H-ZSM-5 obtained by the above method was used instead of the Cu/ZSM-5, and hydrogen/oxygen (pressure ratio: 1/20) was used instead of nitrogen.

Production Example 1 of Aniline from Phenol

Zeolite β (produced by PQ Corporation, CP811BL-25, silica/alumina ratio: 12.5 (molar ratio), nitrogen adsorption specific surface area: 750 m²/g) was used as a catalyst. First, a reaction tube was filled with 0.65 g of the zeolite β. Nitrogen and ammonia gas at a volume ratio of 50:16.6 were allowed to flow through the tube, while the tube was heated in an electric furnace to a predetermined temperature, and then a predetermined amount of phenol was fed by a pump. Here, the reaction conditions were as follows: reaction temperature: 450° C., reaction pressure: normal pressure, feed rate of phenol in terms of LHSV: 1.29/hr, molar feed ratio of ammonia to phenol: 9. After four hours from the start of reaction, a steady state was achieved. Thereafter, a gas-liquid separator was placed at an exit of the reaction tube to collect the resulting reaction liquid. An analysis of the product found that aniline was obtained in a yield of 21.2%. The analysis was performed by gas chromatography (columns: FFAP and CP-WAX). The yield was calculated from the following equation.

Yield (%)=(number of moles of aniline produced per unit time)/(number of moles of phenol fed per unit time)×100

Production Example 2 of Aniline from Phenol

Aniline was obtained in a yield of 84.3% by performing a reaction in the same manner as in Production Example 1, except that the catalyst in Production Example 1 was changed to H-ZSM-5 (produced by Tosoh Corporation, 820 HOA, a calcined product of 820 NHA ($SiO_2/Al_2O_3$=23 (molar ratio), nitrogen adsorption specific surface area: 350 m²/g, crystal size: 0.03 µm×0.1 µm, particle size: 5 µm)), the reaction temperature was changed to 500° C., the pressure was changed to 537 KPa, and the reaction time was changed to eight hours.

Production Example 3 of Aniline from Phenol

Aniline was obtained in a yield of 15.2% by performing a reaction in the same manner as in Production Example 1, except that the ammonia in Production Example 1 was changed to monomethylamine, and the pressure was changed to 2859 KPa.

Production Example 4 of Aniline from Phenol

An alumina catalyst was prepared by mixing a mixture consisting of bayerite (Versal B, produced by LaRoche Chemical) and pseudoboehmite (Versal 900, produced by LaRoche Chemical) at a mass ratio of 4:1 with a 0.4 M aqueous nitric acid solution, and then heating the resulting mixture in a muffle furnace at a temperature of 500° C. for eight hours. Aniline was then obtained in a yield of 46.3% by performing a reaction in the same manner as in Production Example 1, except that the obtained alumina catalyst was used instead, the reaction temperature was changed to 365° C., and the pressure was changed to 1.7 MPa.

Production Example 3 of Antioxidant from Aniline
(Method of Synthesis of Antioxidant TMDQ-3 in Table 2)

To a flask equipped with an acetone introduction device, a distillation device, a thermometer, and a stirrer were added 190 g (2.0 mol) of the aniline obtained above (Synthesis 1 of phenol from biomass material (using microorganism) and Production Example 2 of aniline from phenol) and hydrochloric acid (0.20 mol) as an acidic catalyst, and the mixture was heated to 140° C. Subsequently, 580 g (10 mol) of the acetone obtained above (Method 1-1 of preparing acetone without using petroleum resources) was continuously fed to the reaction system over 6 hours while keeping the temperature at 140° C. Unreacted acetone and aniline that were distilled out were returned to the reaction system as needed. As a result, 180.7 g (yield: about 30%) of polymers of 2,2,4-trimethyl-1,2-dihydroquinoline was obtained. The polymerization degree was 2 to 4. Here, unreacted aniline and 2,2,4-trimethyl-1,2-dihydroquinoline monomer were recovered by reduced-pressure distillation. The unreacted aniline was distilled out at 140° C. By further heating to 190° C., the monomer was distilled out. The amount and yield of the monomer were 19.1 g and 6.9%, respectively.

According to the present method, phenol was synthesized by biosynthesis from a biomass material, and aniline was then highly efficiently synthesized from the thus obtained phenol by using a catalyst. Thus, aniline could be efficiently synthesized while suppressing the total energy consumption and $CO_2$ emission. Furthermore, the combined use of the acetone produced by biosynthesis made it possible to highly efficiently synthesize an antioxidant in an environmentally friendly manner.

Production Example 4 of Antioxidant from Aniline (Method of Synthesis of Antioxidant 6PPD-3 in Table 2)

Two molecules of the acetone synthesized above (Method 1-1 of preparing acetone without using petroleum resources) were subjected to an aldol condensation reaction to synthesize diacetone alcohol. The diacetone alcohol was then easily dehydrated to be converted to mesityl oxide. The mesityl oxide was hydrogenated with a palladium catalyst to synthesize methyl isobutyl ketone.

Aniline was also obtained in the same manner as mentioned above according to (Synthesis 1 of phenol from biomass material (using microorganism)) and (Production Example 2 of aniline from phenol).

An antioxidant 6PPD was synthesized from the obtained aniline, nitrobenzene obtained by oxidation of the aniline by a known method, and the obtained methyl isobutyl ketone by the following method.

An amount of 187 g of a 25% aqueous tetramethylammonium hydroxide solution (TMAOH) was concentrated by distillation at a temperature of 55° C. under a pressure of 75 mbar to give a 35% solution. After addition of the biomass-derived aniline (269 mL) to the solution, the aniline/water azeotrope was evaporated at a temperature of 75° C. under a pressure of 75 mbar until the molar ratio of water/base reached about 4:1. Subsequently, 60 g of the nitrobenzene was added and the resulting mixed solution was further stirred for four hours, while distillation of the water/aniline azeotrope was continued. To the crude mixed solution were added 2.2 g of a Pt/C catalyst (5% Pt) and 120 mL of water. Next, at a temperature of 80° C., the pressure was increased to the maximum of 15 bar with hydrogen, and then the reaction mixture was stirred until no further absorption of hydrogen was found. To the resulting mixture was added 100 mL of toluene, and the catalyst was removed by filtration, followed by separation of the mixture into an organic phase and a water phase with a separatory funnel. Then, purification of the organic phase by fractional distillation gave 4-aminodiphenylamine in a yield of 91%.

An amount of 129.3 g of the 4-aminodiphenylamine, 120.2 g of the methyl isobutyl ketone synthesized above, 0.77 g of a platinum catalyst (5% Pt on carbon sulfide powder (hydrous product), water content: 55.26% by mass, produced by N.E. Chemcat Corporation), and 0.65 g of activated carbon (Taiko activated carbon S-type, produced by Futamura Chemical Co., Ltd.) were introduced into a stirring autoclave and exposed to a hydrogen atmosphere. Then, the inside temperature of the autoclave was raised from room temperature to 150° C. over about one hour. Subsequently, the hydrogen pressure was increased to 30 kgf/cm$^2$ (2.94 MPa), and a reaction was allowed to proceed at the same temperature and the same pressure while feeding the consumed amount of hydrogen.

After two hours from the start of increasing the hydrogen pressure, hydrogen was released from the autoclave to decrease the pressure to normal pressure, while the reaction solution was cooled to room temperature. The reaction solution was filtrated to remove the catalyst and the activated carbon. The resulting reaction product was subjected to separation by high performance liquid chromatography to give 4-(1,3-dimethylbutylamino)diphenylamine (antioxidant 6PPD-3) in a yield of 99.4%.

Production Example 2 of Vulcanization Accelerator MBT from Aniline (Method of Synthesis of Vulcanization Accelerator MBT-3 in Table 2)

An amount of 93 g (1.0 mol) of the aniline obtained above (Synthesis 1 of phenol from biomass material (using microorganism) and Production Example 2 of aniline from phenol), 80 g (1.1 mol) of the carbon disulfide obtained above (Method of preparing carbon disulfide without using petroleum resources), and 16 g (1.0 mol) of sulfur were introduced into a 300-mL pressurized reactor, and subjected to a reaction for two hours at a temperature of 250° C. under a pressure of 10 MPa, followed by cooling to 180° C. Thus, a crude product of 2-mercaptobenzothiazole was obtained in an amount of 130 g (yield: 87%). Moreover, the obtained crude product of 2-mercaptobenzothiazole (purity: 79%) was dissolved in isopropanol at the boiling temperature in an inert gas atmosphere of nitrogen. The resulting mixture was left at room temperature to cool. A precipitated product was separated by filtration, washed with isopropanol, and dried. Thus, a light yellow product (2-mercaptobenzothiazole with high purity (melting point: 180.1° C. to 181.1° C., purity: 98.1%)) was obtained.

Production Example 2 of Vulcanization Accelerator CBS from Aniline (Method of Synthesis of Vulcanization Accelerator CBS-3 in Table 2)

The crude product of 2-mercaptobenzothiazole obtained above was dissolved in an aqueous sodium hydroxide solution to prepare a 20% aqueous solution of a sodium salt of mercaptobenzothiazole. To the solution was added an equivalent molar amount of cyclohexylamine. The mixed solution was further mixed with 100 mL of methanol at a temperature of 40° C. A 13% solution of sodium hypochlorite was allowed to act on the resulting mixture, in an amount of 1.2 times the molar amount of the sodium salt of mercaptobenzothiazole, followed by stirring for one hour. After the reaction, water and the organic solvent were removed so that an oil of N-cyclohexyl-benzothiazolylsulfenamide was obtained (yield: 93%).

(Preparation of Rubber Composition for Tread)

Chemical agents each in an amount shown in Process 1 in Table 2 were introduced into a Banbury mixer and kneaded for 5 minutes to raise the outlet temperature to about 150° C. Thereafter, sulfur and vulcanization accelerators each in an amount shown in Process 2 were added to the kneaded mixture obtained in Process 1, and then kneaded with the Banbury mixer for about three minutes to adjust the outlet temperature to 100° C. Thus, an unvulcanized rubber composition was obtained. The resulting unvulcanized rubber composition was molded into a tread shape, assembled with other tire components and then vulcanized for 20 minutes at a temperature of 170° C. Thus, a test tire was produced.

Furthermore, each unvulcanized rubber composition was vulcanized for 20 minutes at a temperature of 170° C. to prepare a vulcanized rubber sheet.

The chemical agents used above were as follows.

SBR: Nipol NS116 (solution-polymerized SBR, bound styrene content: 21% by mass, Tg: −25° C., produced by ZEON Corporation)
BR: BR150B (cis 1,4 bond content: 97% by mass, $ML_{1+4}$ (100° C.): 40), produced by Ube Industries, Ltd.
NR: RSS #3
Silica: Ultrasil VN2 (BET specific surface area: 125 $m^2/g$), produced by Degussa
Carbon black: Niteron #55S (carbon block made from coal-derived heavy oil, $N_2SA$: $28 \times 10^3$ $m^2/kg$), produced by Nippon Steel Chemical Carbon Co., Ltd.
Silane coupling agent: Si69, produced by Degussa
Mineral oil: PS-32, produced by Idemitsu Kosan Co., Ltd.
Stearic acid: Kiri, produced by NOF Corporation
Zinc oxide: zinc oxide #2, produced by Mitsui Mining & Smelting Co., Ltd.
Antioxidant 6PPD-3: synthesized by the above method
Antioxidant 6PPD-4: Nocrac 6C, produced by Ouchi Shinko Chemical Industrial Co., Ltd.
Antioxidant TMDQ-3: synthesized by the above method
Antioxidant TMDQ-4: Nocrac 224, produced by Ouchi Shinko Chemical Industrial Co., Ltd.
Wax: SUNNOC Wax, produced by Ouchi Shinko Chemical Industrial Co., Ltd.
Sulfur: sulfur powder, produced by Tsurumi Chemical Industry Co., Ltd.
Vulcanization accelerator CBS-3: synthesized by the above method
Vulcanization accelerator CBS-4: Nocceler CZ, produced by Ouchi Shinko Chemical Industrial Co., Ltd.
Vulcanization accelerator MBT-3: synthesized by the above method
Vulcanization accelerator MBT-4: Nocceler M, produced by Ouchi Shinko Chemical Industrial Co., Ltd.

The same evaluations as in Table 1 were made using the thus obtained unvulcanized rubber compositions, vulcanized rubber sheets, and test tires. The test results are shown in Table 2.

The rubber properties including vulcanization properties and breaking energy index, and the tire properties including abrasion resistance, rolling resistance property, and wet/dry grip performance in Example are all equal to those in Comparative Example in which conventional vulcanization accelerators and antioxidants that were synthesized from fossil resources were used. This demonstrated that the Example makes it possible to cope with depletion of fossil resources without any practical problems.

REFERENCE SIGNS LIST

1 Gas introduction pipe
2 Alcohol introduction pipe (material introduction pipe)
3 Reaction tube
4 Alcohol vapor layer (material vapor layer)
5 Catalyst layer (reaction layer)
6 Heater (electric furnace)
7 Product trap
8a Cooling device
8b Heater
9 Fractionator (fractioning pipe)
10 Distillate trap (target product trap)
11 Cooling device
12a, 12b Reactant recirculation line
21 Alcohol introduction pipe (material introduction pipe)
22 Heater
23 Dehydration reaction column
24 Cooling device
25 Heater
26 Aromatic compound synthesis column
27 Cooling device
28 Reactant recirculation line

TABLE 2

| | | | Example | Comparative Example |
|---|---|---|---|---|
| Composition (parts by mass) | Process 1 | SBR | 50 | 50 |
| | | BR | 30 | 30 |
| | | NR | 20 | 20 |
| | | Silica | 75 | 75 |
| | | Carbon black | 5 | 5 |
| | | Silane coupling agent | 6 | 6 |
| | | Mineral oil | 10 | 10 |
| | | Stearic acid | 2 | 2 |
| | | Zinc oxide | 3 | 3 |
| | | Antioxidant 6PPD-3 | 1.5 | |
| | | Antioxidant 6PPD-4 | | 1.5 |
| | | Antioxidant TMDQ-3 | 0.5 | |
| | | Antioxidant TMDQ-4 | | 0.5 |
| | | Wax | 1.5 | 1.5 |
| | Process 2 | Sulfur | 1.5 | 1.5 |
| | | Vulcanization accelerator CBS-3 | 1.5 | |
| | | Vulcanization accelerator CBS-4 | | 1.5 |
| | | Vulcanization accelerator MBT-3 | 0.2 | |
| | | Vulcanization accelerator MBT-4 | | 0.2 |
| Evaluations | Torque rise | | 101 | 100 |
| | Cure time | | 99 | 100 |
| | Breaking energy index | | 100 | 100 |
| | Abrasion resistance index | | 100 | 100 |
| | Rolling resistance index | | 100 | 100 |
| | Wet grip performance index | | 100 | 100 |
| | Dry grip performance index | | 100 | 100 |

What is claimed is:

1. A synthesis method for synthesizing aniline from a biomass material via phenol, said method comprising:
synthesizing the phenol from the biomass resource; and
synthesizing the aniline from the phenol.

2. The synthesis method according to claim 1, wherein the biomass material is a sugar or bioethanol.

3. The synthesis method according to claim 1, wherein the synthesis method is adapted to produce the phenol by a microorganism.

4. The synthesis method according to claim 1, wherein the synthesis method is adapted to produce the phenol by liquid culture of a microorganism.

5. The synthesis method according to claim 3 or 4, wherein the microorganism is resistant to organic solvents.

6. The synthesis method according to claim 1, wherein the synthesis method is adapted to produce the phenol from bioethanol as the biomass material by using a solid acid catalyst.

7. The synthesis method according to claim 6, wherein the solid acid catalyst is a zeolite.

8. The synthesis method according to claim 6, wherein the solid acid catalyst is an MFI zeolite.

9. The synthesis method according to claim 6, wherein the solid acid catalyst is an MFI zeolite carrying a member selected from the group consisting of simple substances of copper, titanium, platinum and ruthenium, and compounds thereof.

10. A rubber chemical for a tire, synthesized from the aniline obtained by the synthesis method according to claim 1.

11. The rubber chemical for a tire according to claim 10, which is synthesized by further using acetone obtained from a biomass material.

12. The rubber chemical for a tire according to claim 11, wherein the acetone is obtained by acetone-butanol fermentation of a sugar by a microorganism.

13. The rubber chemical for a tire according to claim 12, wherein the microorganism is *Clostridium*.

14. The rubber chemical for a tire according to claim 12, wherein the microorganism comprises a gene of *Clostridium* introduced thereinto.

15. The rubber chemical for a tire according to claim 14, wherein the gene encodes acetoacetate decarboxylase, coenzyme A transferase, or thiolase.

16. The rubber chemical for a tire according to claim 11, wherein the acetone is obtained by separation from pyroligneous acid.

17. The rubber chemical for a tire according to claim 11, wherein the acetone is derived from bioethanol.

18. A pneumatic tire produced using the rubber chemical for a tire according to claim 10.

* * * * *